(12) United States Patent
Shen et al.

(10) Patent No.: US 9,657,307 B2
(45) Date of Patent: May 23, 2017

(54) HERBICIDE RESISTANCE GENE AND USE THEREOF

(75) Inventors: Zhicheng Shen, Hangzhou (CN);
Chaoyang Lin, Hangzhou (CN);
Chengyi Liu, Hangzhou (CN)

(73) Assignee: HANGZHOU RUIFENG BIOTECHNOLOGY LIMITED INC., Hangzhou, Zhejiang Province (CN)

( * ) Notice: Subject to any disclaimer, the term of this patent is extended or adjusted under 35 U.S.C. 154(b) by 941 days.

(21) Appl. No.: 13/988,377

(22) PCT Filed: Nov. 16, 2011

(86) PCT No.: PCT/CN2011/082312
§ 371 (c)(1),
(2), (4) Date: Aug. 19, 2013

(87) PCT Pub. No.: WO2012/068966
PCT Pub. Date: May 31, 2012

(65) Prior Publication Data
US 2013/0338007 A1 Dec. 19, 2013

(30) Foreign Application Priority Data
Nov. 22, 2010 (CN) .......................... 2010 1 0556653

(51) Int. Cl.
*C12N 15/82* (2006.01)
*A01H 3/00* (2006.01)
*C07K 14/415* (2006.01)

(52) U.S. Cl.
CPC ........ *C12N 15/8275* (2013.01); *C07K 14/415* (2013.01); *C12N 15/8274* (2013.01)

(58) Field of Classification Search
CPC ............ C12N 15/8274; C12N 15/8275; C07K 14/415
See application file for complete search history.

(56) References Cited

U.S. PATENT DOCUMENTS

2009/0011936 A1* 1/2009 Hawkes ............... C12N 9/0077
504/136

OTHER PUBLICATIONS

Zhang, Lei, et al. "Identification of a cytochrome P450 hydroxylase, CYP81A6, as the candidate for the bentazon and sulfonylurea herbicide resistance gene, Bel, in rice." Molecular Breeding 19.1 (2007): 59-68.*
Saika, Hiroaki, et al. "A novel rice cytochrome P450 gene, CYP72A31, confers tolerance to acetolactate synthase-inhibiting herbicides in rice and Arabidopsis." Plant physiology 166.3 (2014): 1232-1240.*

* cited by examiner

*Primary Examiner* — Amjad Abraham
*Assistant Examiner* — Fan Weihua
(74) *Attorney, Agent, or Firm* — Womble Carlyle Sandridge & Rice LLP

(57) ABSTRACT

Disclosed are a herbicide resistance gene and use thereof, wherein 1) the amino acid sequence of the encoded protein is at least more than 80% identical to SEQ ID NO:1; and 2) the encoded protein is capable of resulting in resistance to at least one of the following types of herbicides: acetolactate synthase (ALS)-inhibiting herbicides, protoporphyrinogen oxidase (PPO)-inhibiting herbicides, p-hydroxyphenylpyruvate dioxygenase (HPPD)-inhibiting herbicides, photosystem II-inhibiting herbicides, and synthetic auxin herbicides. The gene disclosed herein can be introduced into a plant to obtain a transgenic plant against herbicides. A method is disclosed for obtaining an herbicide-resistant transgenic plant by using an herbicide-resistant gene. Such herbicide-resistant transgenic plant can prevent damage of herbicides to the plant, providing a convenient and economical means for selectively killing weeds.

12 Claims, 1 Drawing Sheet

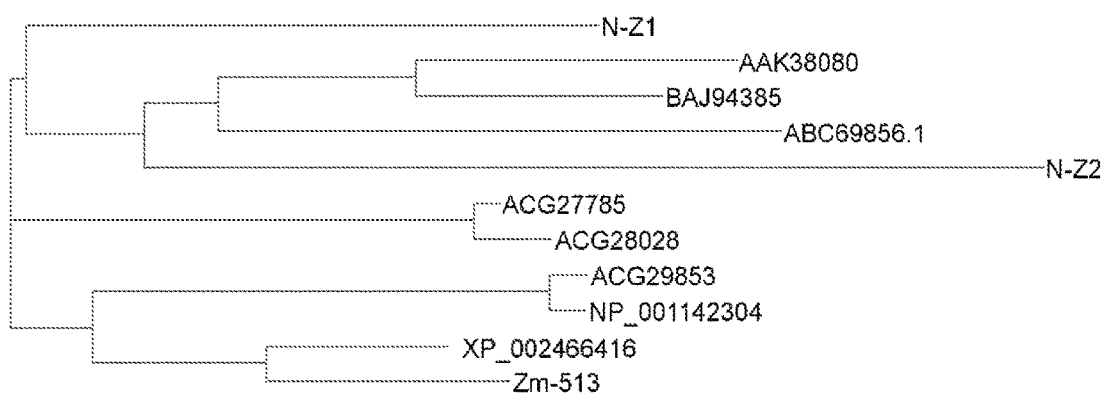

SEQUENCE LISTING

```
<160> NUMBER OF SEQ ID NOS: 19

<210> SEQ ID NO 1
<211> LENGTH: 517
<212> TYPE: PRT
<213> ORGANISM: Cynodon dactylon

<400> SEQUENCE: 1

Met Asp Lys Ala Tyr Val Ala Leu Leu Ser Phe Ala Ser Leu Phe Leu
1               5                   10                  15

Leu His Tyr Leu Val Ser Arg Arg Asn Gly Thr Gly Lys Gly Ser Lys
            20                  25                  30

Ala Lys Gly Ala Leu Pro Pro Ser Pro Pro Ser Val Pro Phe Leu Gly
        35                  40                  45

His Leu His Leu Val Lys Thr Pro Phe His Ala Ala Leu Ala Arg Leu
    50                  55                  60

Ala Asp Cys His Gly Pro Val Phe Ser Leu Arg Met Gly Ala Arg Pro
65                  70                  75                  80
```

```
Ala Val Val Val Ser Ser Pro Glu His Ala Lys Glu Cys Phe Thr Glu
                85                  90                  95

His Asp Val Ala Phe Ala Asn Arg Pro Arg Phe Pro Ser Gln Gln Leu
            100                 105                 110

Ala Ser Phe Asn Gly Ala Ala Leu Gly Ser Ala Ser Tyr Gly Pro Tyr
            115                 120                 125

Trp Arg Asn Leu Arg Arg Val Ala Thr Val His Leu Leu Ser Ala His
130                 135                 140

Arg Val Ala Cys Met Thr Gly Thr Ile Ala Ala Glu Val Arg Ala Met
145                 150                 155                 160

Val Arg Arg Met Asn Arg Ala Ala Gln Val Ala Ser Gly Gly Ala Ala
                165                 170                 175

Arg Ile Glu Leu Lys Arg Arg Leu Phe Glu Val Ser Leu Ser Val Leu
                180                 185                 190

Met Glu Thr Ile Ala Arg Thr Lys Thr Ser Arg Thr Glu Ala Asp Asp
                195                 200                 205

Asp Thr Asp Met Ser Pro Glu Ala Arg Glu Phe Lys Gln Ile Val Asp
    210                 215                 220

Glu Leu Leu Pro His Leu Gly Thr Ala Asn Leu Trp Asp Tyr Met Pro
225                 230                 235                 240

Val Leu Arg Trp Phe Asp Val Phe Gly Val Arg Lys Lys Ile Val Ser
                245                 250                 255

Ala Val Arg Arg Asp Ala Phe Leu Arg His Leu Val Asp Ala Glu
                260                 265                 270

Arg Thr Arg Leu Asp Asp Gly Asn Asp Ala Gly Glu Lys Lys Ser Ile
            275                 280                 285

Ile Ala Met Leu Leu Thr Leu Gln Lys Ser Glu Pro Asp Val Tyr Ser
            290                 295                 300

Asp Thr Met Ile Met Ala Leu Cys Gly Asn Leu Phe Gly Ala Gly Thr
305                 310                 315                 320

Glu Thr Thr Ser Thr Thr Thr Glu Trp Ala Met Ser Leu Leu Leu Asn
                325                 330                 335

His Pro Glu Lys Leu Arg Lys Ala Gln Ala Glu Ile Asp Ala Val Val
            340                 345                 350

Gly Thr Ser Arg Leu Leu Thr Ala Asp Asp Met Pro Arg Leu Thr Tyr
            355                 360                 365

Leu Arg Cys Ile Ile Asp Glu Thr Met Arg Leu Tyr Pro Ala Ala Pro
            370                 375                 380

Leu Leu Leu Pro His Glu Ser Ser Thr His Cys Lys Val Gly Gly Tyr
385                 390                 395                 400

Asp Val Pro Ala Gly Thr Met Leu Leu Val Asn Val Tyr Ala Ile His
                405                 410                 415

Arg Asp Pro Ala Val Trp Asp Gly Pro Thr Glu Phe Val Pro Glu Arg
            420                 425                 430

Phe Glu Asp Gly Lys Ala Glu Gly Arg Leu Leu Met Pro Phe Gly Met
            435                 440                 445

Gly Arg Arg Lys Cys Pro Gly Glu Thr Leu Ala Leu Arg Thr Ile Gly
450                 455                 460

Leu Val Leu Gly Thr Leu Ile Gln Cys Phe Asp Trp Asp Arg Val Asp
465                 470                 475                 480

Gly Leu Glu Val Asp Met Thr Glu Ser Gly Gly Leu Thr Ile Pro Arg
                485                 490                 495
```

Ala Val Pro Leu Glu Ala Met Cys Arg Pro Arg Ala Thr Met Arg Glu
                500                 505                 510

Val Leu Gln Glu Leu
        515

<210> SEQ ID NO 2
<211> LENGTH: 1554
<212> TYPE: DNA
<213> ORGANISM: Cynodon dactylon

<400> SEQUENCE: 2

| | | | | | |
|---|---|---|---|---|---|
| atggataagg | cctacgtggc | cctcctctcc | ttcgcctccc | tcttcttgct | ccactacctc | 60 |
| gtttcccgcc | gcaatggcac | cgggaagggc | agcaaggcca | agggcgcgct | gccgccaagc | 120 |
| cctccatccg | ttccgttcct | gggccaccatc | caccttgtca | agacgccatt | ccacgctgcg | 180 |
| ctggcacgcc | tcgcggactg | ccacggcccg | gtcttctccc | tgcggatggg | agcccgcccc | 240 |
| gcagttgtgg | tgtcctcgcc | ggagcacgcc | aaggagtgct | tcacggagca | cgacgtggcc | 300 |
| ttcgccaacc | ggccgcgctt | ccctcgcag | cagctcgcct | ccttcaacgg | tgccgcgctg | 360 |
| ggttccgcca | gctacggccc | gtactggcgc | aacctccgcc | gcgtcgccac | cgtccacctc | 420 |
| ctgtccgcgc | accgcgtcgc | gtgcatgacg | gggactatcg | cggccgaggt | gcgggccatg | 480 |
| gtgcgacgga | tgaaccgcgc | gcgcgcaggtg | gcatcaggcg | gcgcggcgcg | catcgagctc | 540 |
| aagcggaggc | tatttgaggt | ctcgctcagc | gtgcttatgg | agaccatcgc | gcggaccaag | 600 |
| acgtcacgta | cggaggcgga | cgacgacacg | gacatgtcgc | ctgaggcccg | ggagttcaag | 660 |
| cagatcgtgg | atgagctcct | gcctcacctc | ggcacggcta | acttgtggga | ctacatgccg | 720 |
| gtgttgcggt | ggttcgacgt | gttcggcgtg | aggaagaaga | tcgtgtccgc | ggtgaggaga | 780 |
| agggacgcgt | tcctgcggca | tcttgtcgac | gcagagagga | cgaggctgga | cgacggcaac | 840 |
| gatgcgggcg | agaagaagag | catcattgct | atgctgctca | ctctgcagaa | gtcagagccg | 900 |
| gacgtctact | cggataccat | gatcatggct | ctatgtggga | acttgtttgg | ggccggcaca | 960 |
| gagaccacgt | cgacgaccac | cgaatgggcc | atgtctctcc | tcctcaacca | cccggagaag | 1020 |
| ctcaggaagg | cgcaggctga | gatcgatgct | gtcgtgggca | catcccgcct | tcttaccgcc | 1080 |
| gacgacatgc | ctcgtctcac | ctacctccgc | tgcatcatcg | acgagaccat | gcgcctgtac | 1140 |
| ccggccgcac | cacttctgct | gccacacgag | tcctcgacac | actgcaaggt | cggcggctac | 1200 |
| gacgtgcccg | ccggcacgat | gctgctcgtc | aacgtgtacg | ccatccacag | ggaccccgcg | 1260 |
| gtgtgggacg | ggccgaccga | gttcgtgccg | gagcggttcg | aggatggcaa | ggcagaaggc | 1320 |
| cggctgctga | tgccgttcgg | gatgggacgg | cgcaagtgtc | ccggcgagac | gctcgcgctg | 1380 |
| cggacgatcg | ggctggtgct | cggcacgctg | atccagtgtt | tcgactggga | ccgggttgat | 1440 |
| ggtcttgagg | tcgacatgac | tgaaagtggt | gggctcacga | tccccagggc | tgtcccgttg | 1500 |
| gaggccatgt | gcaggcctcg | tgcgacgatg | cgtgaggttt | tgcaggagct | ctga | 1554 |

<210> SEQ ID NO 3
<211> LENGTH: 531
<212> TYPE: PRT
<213> ORGANISM: Cynodon dactylon

<400> SEQUENCE: 3

Met Asp Lys Ala Tyr Val Ala Ile Val Leu Ser Ile Leu Phe Leu Phe
 1               5                  10                  15

Ser Ile Gln Arg Phe Leu Gly His Arg Arg Arg Ser Arg Ser Asn Val
            20                  25                  30

-continued

Asp Asn Gly Lys Asn Lys Ser Val Thr His Asn Arg Leu Pro Pro Gly
            35                  40                  45

Pro Arg Ala Val Pro Val Leu Gly His Leu His Leu Leu Lys Lys Pro
 50                  55                  60

Ile His Ala Ala Leu Ala Arg Leu Ala Ser Gln His Gly Pro Leu Phe
 65                  70                  75                  80

Ser Leu Arg Leu Gly Ser Arg Pro Ala Val Val Thr Ser Ala Glu
                85                  90                  95

Leu Ala Arg Glu Cys Phe Thr Glu His Asp Val Thr Phe Ala Thr Arg
                100                 105                 110

Pro Arg Phe Ala Ser Leu Asp Leu Val Ser Phe Gly Thr Thr Leu
            115                 120                 125

Pro Thr Ser Arg Tyr Gly Pro Tyr Trp Arg Asn Leu Arg Arg Val Ala
            130                 135                 140

Thr Val His Leu Leu Ser Ala His Arg Val Gly Cys Met Leu Pro Val
145                 150                 155                 160

Val Ser Ser Glu Val Arg Ala Met Ala Arg Arg Val Tyr Arg Ala Ala
                165                 170                 175

Ala Ala Ala Pro Arg Gly Ala Ala Arg Val Glu Leu Lys Arg Arg Leu
            180                 185                 190

Phe Glu Leu Ser Leu Ser Ala Leu Met Glu Thr Ile Ala Arg Thr Lys
            195                 200                 205

Thr Ser Arg Ala Glu Ala Asp Asp Arg Asp Met Ser Pro Glu Thr
210                 215                 220

Gln Glu Phe Lys Glu Ala Leu Asp Glu Phe Ile Pro Leu Ile Gly Ala
225                 230                 235                 240

Ala Asn Val Trp Asp Phe Leu Pro Leu Leu Arg Trp Leu Asp Val Phe
            245                 250                 255

Gly Val Arg Arg Lys Ile Leu Ala Ala Val Ser Arg Arg Asp Ala Phe
            260                 265                 270

Leu Gln Arg Leu Ile Asp Ala Glu Arg Arg Leu Gly Asp Asp Asn
            275                 280                 285

Ser Cys Asn Asp Gly Ser Asp Lys Lys Ser Met Ile Ala Val Leu Leu
    290                 295                 300

Asn Leu Gln Lys Thr Glu Pro Glu Val Tyr Thr Asp Ala Thr Ile Met
305                 310                 315                 320

Ala Leu Cys Thr Ser Met Phe Thr Gly Gly Ala Glu Thr Thr Ala Thr
            325                 330                 335

Thr Thr Glu Trp Ala Met Ser Leu Leu Leu Asn His Pro Asp Val Leu
            340                 345                 350

Lys Lys Ala Gln Ala Glu Met Asp Val Ser Val Gly Thr Ser Arg Leu
            355                 360                 365

Val Thr Ala Ala Asp Val Pro His Leu Gly Tyr Leu Gln Cys Ile Ile
    370                 375                 380

Ser Glu Thr Leu Arg Leu Tyr Pro Ala Val Pro Thr Leu Val Pro His
385                 390                 395                 400

Glu Ser Thr Ala Asp Cys Val Ile Gly Gly His His Val Pro Ala
                405                 410                 415

Gly Thr Met Leu Leu Val Asn Gly Tyr Ala Ile His Arg Asp Pro Ala
            420                 425                 430

Thr Trp Pro Asp Pro Ala Ala Phe Arg Pro Glu Arg Phe Glu Asp Gly
            435                 440                 445

```
Lys Ala Glu Gly Lys Phe Ile Ile Thr Phe Gly Met Gly Arg Arg Lys
    450                 455                 460
Cys Pro Gly Glu Thr Leu Ala Leu Arg Thr Ile Gly Leu Val Leu Gly
465                 470                 475                 480
Met Leu Ile Gln Cys Phe Asp Trp Asp Thr Ala Asp Gly Gly Lys Val
                485                 490                 495
Asp Met Thr Glu Gly Val Gly Ile Thr Leu Pro Arg Ala Val Pro Leu
            500                 505                 510
Glu Ala Met Cys Arg Pro Arg Gln Thr Met Val Asp Val Leu Lys Gly
        515                 520                 525
Leu Leu Glu
    530

<210> SEQ ID NO 4
<211> LENGTH: 1596
<212> TYPE: DNA
<213> ORGANISM: Cynodon dactylon

<400> SEQUENCE: 4
```

| | | |
|---|---|---|
| atggataagg cctacgtggc catcgtcctc tccatcctct tcctcttctc catccaacga | 60 |
| tttctcggcc accgtcgtcg cagtcgcagc aacgtcgaca atggcaagaa caagtcggta | 120 |
| acacataacc gtctgccacc gggtccacgt gccgtcccgg tcctcggcca cctccacctc | 180 |
| ctcaagaagc ccatccacgc cgctctcgcg cgcctcgcct cgcaacacgg cccgctcttc | 240 |
| tccctccgcc tggggtcccg ccccgcggtg gtcgtgacct ccgctgagct cgccagggaa | 300 |
| tgcttcacgg agcacgatgt gacgttcgcg accggccgc gcttcgcctc tctcgacctc | 360 |
| gtctccttcg gcgggaccac gctcccgacc tcgcgctacg gccctactg cgcaaccctc | 420 |
| cgccgtgtgg ccaccgtgca cctcctctcc gcgcaccgcg tgggctgcat gctccccgtc | 480 |
| gtctccagcg aggtgcgcgc catggcgcgg cgggtgtacc gcgccgccgc ggccgcacca | 540 |
| cgtggcgcgg cgagggtgga gttgaagcgg aggctgttcg agctctcgct cagcgcgctg | 600 |
| atggagacca tcgcaaggac caagacgtcc cgtgccgagg ctgacgccga cagggacatg | 660 |
| tcgccggaga cgcaggagtt caaggaggcg ctggacgagt tcatcccgct gatcggcgcg | 720 |
| gccaacgtgt gggacttctt gccgctgctg cggtggctcg acgtgttcgg cgtgaggagg | 780 |
| aagatcctgg ctgccgtgag caggagggac gcgtttctcc agcggctcat cgacgcagag | 840 |
| cggcggaggc ttggtgatga taatagctgc aatgatggta gcgacaagaa gagcatgatc | 900 |
| gccgtgctgc tgaacctgca aaagacagag ccggaggtgt acacggatgc caccatcatg | 960 |
| gcgctatgca ccagcatgtt caccggggga gcagagacta cggcgaccac gaccgaatgg | 1020 |
| gcgatgtccc tgctgctaaa ccaccccgat gttctcaaaa aagcgcaggc agagatggac | 1080 |
| gtttccgtgg gcacctcacg cctggtcacc gccgccgacg tgccgcacct cggctacctc | 1140 |
| caatgcatca tcagcgagac gctccgcctg tacccggccg tcccgacgct ggtgccgcac | 1200 |
| gagtccacgg ccgactgcgt cattggcggc accaccatg tgccggcagg cacgatgctg | 1260 |
| ctcgtcaacg gatacgccat ccatagggat ccggcgacgt ggccggaccc ggccgcgttc | 1320 |
| cggccagagc ggttcgagga cggtaaggcc gagggcaagt tcataatcac gttcgggatg | 1380 |
| ggcggcgca agtgtcccgg cgagacgctc gcgttgcgga ccattgggct ggtgctgggc | 1440 |
| atgctgatcc agtgcttcga ctgggacacg gctgatggcg gcaaggttga tatgactgaa | 1500 |
| ggggtcggga tcacgctccc cagggctgtt ccgttggaag ccatgtgcag gccgcgccag | 1560 |
| accatggttg atgttctcaa ggggctgctc gagtaa | 1596 |

<210> SEQ ID NO 5
<211> LENGTH: 1566
<212> TYPE: DNA
<213> ORGANISM: Zea mays

<400> SEQUENCE: 5

```
atggataagg cctacatcgc cgccctctcc gccgccgccc tcttcttgct ccactacctc      60
ctgggccgcc gggccggcgg cgagggcaag gccaaggcca agggctcgcg gcggcggctc     120
ccgccgagcc ctccggcgat cccgttcctg ggccacctcc acctcgtcaa ggccccgttc     180
cacggggcgc tggcccgcct cgcggcgcgc acggcccgg tgttctccat cgcctgggg      240
acccggcgcg ccgtggtcgt gtcgtcgccg gactgcgcca gggagtgctt cacggagcac     300
gacgtgaact cgcgaaccg gccgctgttc ccgtcgatgc ggctggcgtc cttcgacggc     360
gccatgctct ccgtgtccag ctacggcccg tactggcgca acctgcgccg cgtcgccgcc     420
gtgcagctcc tctccgcgca ccgcgtcggg tgcatggccc ccgccatcga agcgcaggtg     480
cgcgccatgg tgcggaggat ggaccgcgcc gccgcggccg gcggcggcgg cgtcgcgcgc     540
gtccagctca agcggcggct gttcgagctc tccctcagcg tgctcatgga gaccatcgcg     600
cacaccaaga cgtcccgcgc cgaggccgac gccgactcgg acatgtcgac cgaggcccac     660
gagttcaagc agatcgtcga cgagctcgtg ccgtacatcg gcacggccaa ccgctgggac     720
tacctgccgg tgctgcgctg gttcgacgtg ttcggcgtga ggaacaagat cctcgacgcc     780
gtgggcagaa gggacgcgtt cctggggcgg ctcatcgacg gggagcggcg gaggctggac     840
gctggcgacg agagcgaaag taagagcatg attgcggtgc tgctcactct gcagaagtcc     900
gagccagagg tctacactga cactgtgatc actgctcttt gcgcgaacct attcggcgcc     960
ggaacggaga ccacgtccac cacgacggaa tgggccatgt cactgctgct gaaccaccgg    1020
gaggcgctca agaaggcgca ggccgagatc gacgcggcgg tgggcacctc ccgcctggtg    1080
accgcggacg acgtgcccca cctcacctac ctgcagtgca tcgtcgacga cgcgctgcgc    1140
ctgcacccgg ccgcgccgct gctgctgccg cacgagtccg ccgcggactg cacggtcggc    1200
ggctacgacg tgccgcgcgg cacgatgctg ctggtcaacg tgcacgcggt ccacagggac    1260
cccgcggtgt gggaggaccc ggacaggttc gtgccggagc ggttcgaggg cgccggcggc    1320
aaggccgagg ggcgcctgct gatgccgttc gggatggggc ggcgcaagtg ccccggggag    1380
acgctcgcgc tgcggaccgt cgggctggtg ctcgccacgc tgctccagtg cttcgactgg    1440
gacacggttg atggagctca ggttgacatg aaggctagcg gcgggctgac catgccccgg    1500
gccgtcccgt tggaggccat gtgcaggccg cgtacagcta tgcgtggtgt tcttaagagg    1560
ctctga                                                               1566
```

<210> SEQ ID NO 6
<211> LENGTH: 521
<212> TYPE: PRT
<213> ORGANISM: Zea mays

<400> SEQUENCE: 6

Met Asp Lys Ala Tyr Ile Ala Ala Leu Ser Ala Ala Leu Phe Leu
1               5                   10                  15

Leu His Tyr Leu Leu Gly Arg Arg Ala Gly Gly Glu Gly Lys Ala Lys
            20                  25                  30

Ala Lys Gly Ser Arg Arg Arg Leu Pro Pro Ser Pro Pro Ala Ile Pro
        35                  40                  45

```
Phe Leu Gly His Leu His Leu Val Lys Ala Pro Phe His Gly Ala Leu
 50                  55                  60
Ala Arg Leu Ala Ala Arg His Gly Pro Val Phe Ser Met Arg Leu Gly
 65                  70                  75                  80
Thr Arg Arg Ala Val Val Val Ser Ser Pro Asp Cys Ala Arg Glu Cys
                 85                  90                  95
Phe Thr Glu His Asp Val Asn Phe Ala Asn Arg Pro Leu Phe Pro Ser
            100                 105                 110
Met Arg Leu Ala Ser Phe Asp Gly Ala Met Leu Ser Val Ser Ser Tyr
            115                 120                 125
Gly Pro Tyr Trp Arg Asn Leu Arg Arg Val Ala Ala Val Gln Leu Leu
130                 135                 140
Ser Ala His Arg Val Gly Cys Met Ala Pro Ala Ile Glu Ala Gln Val
145                 150                 155                 160
Arg Ala Met Val Arg Arg Met Asp Ala Ala Ala Gly Gly Gly
                165                 170                 175
Gly Val Ala Arg Val Gln Leu Lys Arg Arg Leu Phe Glu Leu Ser Leu
            180                 185                 190
Ser Val Leu Met Glu Thr Ile Ala His Thr Lys Thr Ser Arg Ala Glu
            195                 200                 205
Ala Asp Ala Asp Ser Asp Met Ser Thr Glu Ala His Glu Phe Lys Gln
210                 215                 220
Ile Val Asp Glu Leu Val Pro Tyr Ile Gly Thr Ala Asn Arg Trp Asp
225                 230                 235                 240
Tyr Leu Pro Val Leu Arg Trp Phe Asp Val Phe Gly Val Arg Asn Lys
                245                 250                 255
Ile Leu Asp Ala Val Gly Arg Arg Asp Ala Phe Leu Gly Arg Leu Ile
            260                 265                 270
Asp Gly Glu Arg Arg Arg Leu Asp Ala Gly Asp Glu Ser Glu Ser Lys
            275                 280                 285
Ser Met Ile Ala Val Leu Leu Thr Leu Gln Lys Ser Glu Pro Glu Val
290                 295                 300
Tyr Thr Asp Thr Val Ile Thr Ala Leu Cys Ala Asn Leu Phe Gly Ala
305                 310                 315                 320
Gly Thr Glu Thr Thr Ser Thr Thr Glu Trp Ala Met Ser Leu Leu
                325                 330                 335
Leu Asn His Arg Glu Ala Leu Lys Lys Ala Gln Ala Glu Ile Asp Ala
            340                 345                 350
Ala Val Gly Thr Ser Arg Leu Val Thr Ala Asp Val Pro His Leu
            355                 360                 365
Thr Tyr Leu Gln Cys Ile Val Asp Glu Thr Leu Arg Leu His Pro Ala
370                 375                 380
Ala Pro Leu Leu Leu Pro His Glu Ser Ala Ala Asp Cys Thr Val Gly
385                 390                 395                 400
Gly Tyr Asp Val Pro Arg Gly Thr Met Leu Leu Val Asn Val His Ala
                405                 410                 415
Val His Arg Asp Pro Ala Val Trp Glu Asp Pro Asp Arg Phe Val Pro
            420                 425                 430
Glu Arg Phe Glu Gly Ala Gly Gly Lys Ala Glu Gly Arg Leu Leu Met
            435                 440                 445
Pro Phe Gly Met Gly Arg Arg Lys Cys Pro Gly Glu Thr Leu Ala Leu
450                 455                 460
```

```
Arg Thr Val Gly Leu Val Leu Ala Thr Leu Leu Gln Cys Phe Asp Trp
465                 470                 475                 480

Asp Thr Val Asp Gly Ala Gln Val Asp Met Lys Ala Ser Gly Gly Leu
                485                 490                 495

Thr Met Pro Arg Ala Val Pro Leu Glu Ala Met Cys Arg Pro Arg Thr
            500                 505                 510

Ala Met Arg Gly Val Leu Lys Arg Leu
            515                 520
```

<210> SEQ ID NO 7
<211> LENGTH: 522
<212> TYPE: PRT
<213> ORGANISM: Sorghum bicolor

<400> SEQUENCE: 7

```
Met Asp Lys Ala Tyr Val Ala Val Leu Ser Phe Ala Phe Leu Phe Val
1               5                   10                  15

Leu His Tyr Leu Val Gly Arg Ala Gly Gly Asn Gly Arg Lys Gly Asn
                20                  25                  30

Asn Gly Lys Gly Asn Ala Ala Gln Gln Arg Leu Pro Pro Ser Pro Pro
                35                  40                  45

Ala Val Pro Phe Leu Gly His Leu His Leu Val Lys Thr Pro Phe His
            50                  55                  60

Glu Ala Leu Ala Gly Leu Ala Ala Arg His Gly Pro Val Phe Ser Met
65                  70                  75                  80

Arg Met Gly Ser Arg Gly Ala Val Val Ser Ser Pro Glu Cys Ala
                85                  90                  95

Lys Glu Cys Phe Thr Glu His Asp Val Ala Phe Ala Asn Arg Pro Arg
                100                 105                 110

Phe Ala Thr Gln Glu Leu Val Ser Phe Gly Gly Ala Ala Leu Ala Thr
                115                 120                 125

Ala Ser Tyr Gly Pro Tyr Trp Arg Asn Leu Arg Arg Val Ala Ala Val
            130                 135                 140

Gln Leu Leu Ser Ala His Arg Val Ala Cys Met Ser Ser Val Ile Ser
145                 150                 155                 160

Ala Glu Val Arg Ala Met Val Arg Arg Met Ser Arg Ala Ala Ala Ala
                165                 170                 175

Ala Pro Asp Gly Ala Arg Val Gln Leu Lys Arg Arg Leu Phe Glu
            180                 185                 190

Val Ser Leu Ser Val Leu Met Glu Thr Ile Ala Gln Thr Lys Thr Ser
                195                 200                 205

Arg Thr Glu Ala Asp Ala Asp Thr Asp Met Ser Pro Glu Ala His Glu
            210                 215                 220

Phe Lys Gln Ile Val Asp Glu Ile Val Pro His Leu Gly Thr Ala Asn
225                 230                 235                 240

Leu Trp Asp Tyr Leu Pro Val Leu Gln Trp Phe Asp Val Phe Gly Val
                245                 250                 255

Arg Asn Lys Ile Met Ala Ala Val Ser Arg Arg Asp Ala Phe Leu Arg
                260                 265                 270

Arg Leu Ile Asp Ala Glu Arg Arg Met Asp Asp Gly Gly Asp Ser
            275                 280                 285

Asp Lys Lys Ser Met Ile Ala Val Leu Leu Ser Leu Gln Lys Ser Glu
            290                 295                 300

Pro Glu Leu Tyr Thr Asp Thr Met Ile Met Ala Leu Cys Gly Asn Leu
305                 310                 315                 320
```

```
Phe Gly Ala Gly Thr Glu Thr Thr Ser Ser Thr Thr Glu Trp Ala Met
                325                 330                 335

Ser Leu Leu Leu Asn His Pro Glu Ala Leu Lys Lys Ala Gln Ala Glu
            340                 345                 350

Ile Asp Ala Val Val Gly Asn Ser Arg Leu Ile Thr Ala Glu Asp Val
        355                 360                 365

Pro Arg Leu Gly Tyr Leu Gln Cys Val Ile Asn Glu Thr Leu Arg Met
    370                 375                 380

Tyr Pro Ala Ala Pro Leu Leu Pro His Glu Ser Ala Ala Asp Cys
385                 390                 395                 400

Lys Val Gly Gly Tyr Asp Val Pro Arg Gly Thr Leu Leu Ile Val Asn
            405                 410                 415

Ala Tyr Ala Ile His Arg Asp Pro Ala Val Trp Glu Asp Pro Ala Glu
        420                 425                 430

Phe Arg Pro Glu Arg Phe Glu Asp Gly Lys Ala Glu Gly Arg Leu Leu
    435                 440                 445

Met Pro Phe Gly Met Gly Arg Arg Lys Cys Pro Gly Glu Thr Leu Ala
450                 455                 460

Leu Arg Thr Val Gly Leu Val Leu Gly Thr Leu Ile Gln Cys Ile Asp
465                 470                 475                 480

Trp Asp Arg Val Asp Gly Leu Glu Ile Asp Met Thr Ala Gly Gly
                485                 490                 495

Leu Thr Met Pro Arg Ala Val Pro Leu Glu Ala Thr Cys Lys Pro Arg
            500                 505                 510

Ala Ala Met Arg Asp Val Leu Met Glu Leu
            515                 520

<210> SEQ ID NO 8
<211> LENGTH: 518
<212> TYPE: PRT
<213> ORGANISM: Hordeum vulgare

<400> SEQUENCE: 8

Met Asp Lys Ala Tyr Ile Ala Ile Leu Thr Ile Val Phe Leu Phe Leu
1               5                   10                  15

Leu His Tyr Ile Leu Arg Arg Val Ser Asn Gly Arg Gly Lys Gly
            20                  25                  30

Ala Val Gln Leu Pro Ser Pro Pro Ala Val Pro Phe Leu Gly His
        35                  40                  45

Leu His Leu Leu Glu Lys Pro Phe His Ala Ala Leu Gly Arg Leu Ala
    50                  55                  60

Ala Arg Leu Gly Pro Val Phe Ser Leu Arg Leu Gly Ser Arg Ala
65                  70                  75                  80

Val Val Val Ser Ser Ala Glu Cys Ala Arg Glu Cys Phe Thr Glu His
                85                  90                  95

Asp Val Thr Phe Ala Asn Arg Pro Arg Phe Pro Ser Gln Leu Leu Val
            100                 105                 110

Ser Phe Asn Gly Ala Ala Leu Ala Thr Ser Ser Tyr Gly Pro His Trp
        115                 120                 125

Arg Asn Leu Arg Arg Val Ala Val Gln Leu Leu Ser Ala His Arg
    130                 135                 140

Val Ala Cys Met Ser Gly Val Ile Ala Gly Glu Val Arg Ala Met Ala
145                 150                 155                 160

Arg Arg Leu Phe Arg Ala Ala Glu Ala Ser Pro Gly Gly Gly Gly Ala
                165                 170                 175
```

```
Ala Arg Val Gln Leu Lys Arg Arg Leu Phe Glu Leu Ser Leu Ser Val
            180                 185                 190

Leu Met Glu Thr Ile Ala Gln Thr Lys Gly Thr Arg Ser Glu Ala Asp
        195                 200                 205

Ala Asp Thr Asp Met Ser Val Glu Ala Gln Glu Phe Lys Lys Val Val
        210                 215                 220

Asp Glu Ile Ile Pro Tyr Leu Gly Ala Ala Asn Thr Trp Asp Tyr Leu
225                 230                 235                 240

Pro Val Met Arg Trp Phe Asp Val Phe Gly Val Arg Asn Lys Ile Leu
                245                 250                 255

Ala Ala Val Ser Arg Arg Asp Ala Phe Leu His Arg Leu Ile Asp Ala
            260                 265                 270

Glu Arg Arg Leu Asp Gly Gly Ala Glu Ala Asp Lys Lys Ser
        275                 280                 285

Met Ile Ala Val Leu Leu Thr Leu Gln Lys Thr Glu Pro Glu Val Tyr
        290                 295                 300

Thr Asp Thr Met Ile Thr Ala Leu Cys Ala Asn Leu Phe Gly Ala Gly
305                 310                 315                 320

Thr Glu Thr Thr Ser Ser Thr Thr Glu Trp Ala Met Ser Leu Leu Leu
                325                 330                 335

Asn His Pro Ala Ala Leu Arg Lys Ala Gln Ala Glu Ile Asp Val Ala
            340                 345                 350

Val Gly Thr Ser Arg Leu Val Thr Ala Asp Val Pro Arg Leu Ala
        355                 360                 365

Tyr Leu Gln Cys Ile Val Ser Glu Thr Leu Arg Leu Tyr Pro Ala Ala
        370                 375                 380

Pro Met Leu Leu Pro His Gln Ser Ser Ala Asp Cys Lys Val Gly Gly
385                 390                 395                 400

Tyr Asn Val Pro Ser Gly Thr Met Leu Met Val Asn Ala Tyr Ala Ile
                405                 410                 415

His Arg Asp Pro Ala Ala Trp Glu Arg Pro Leu Glu Phe Val Pro Glu
            420                 425                 430

Arg Phe Glu Asp Gly Lys Ala Glu Gly Arg Phe Met Ile Pro Phe Gly
        435                 440                 445

Met Gly Arg Arg Cys Pro Gly Glu Thr Leu Ala Leu Arg Thr Ile
        450                 455                 460

Gly Met Val Leu Ala Thr Leu Val Gln Cys Phe Asp Trp Asp Arg Val
465                 470                 475                 480

Asp Gly Lys Glu Val Asp Met Thr Glu Ser Gly Gly Leu Thr Ile Pro
                485                 490                 495

Lys Ala Val Pro Leu Glu Ala Val Cys Arg Pro Arg Ala Ala Met Arg
            500                 505                 510

Asp Val Leu Gln Ser Leu
        515

<210> SEQ ID NO 9
<211> LENGTH: 517
<212> TYPE: PRT
<213> ORGANISM: Lolium rigidum

<400> SEQUENCE: 9

Met Asp Lys Ala Tyr Ile Ala Ile Leu Ser Cys Ala Phe Leu Phe Leu
1               5                   10                  15

Val His Tyr Val Leu Gly Lys Val Ser Asp Gly Arg Arg Gly Lys Lys
            20                  25                  30
```

-continued

```
Gly Ala Val Gln Leu Pro Pro Ser Pro Pro Ala Val Pro Phe Leu Gly
             35                  40                  45
His Leu His Leu Val Asp Lys Pro Ile His Ala Thr Met Cys Arg Leu
 50                  55                  60
Ala Ala Arg Leu Gly Pro Val Phe Ser Leu Arg Leu Gly Ser Arg Arg
 65                  70                  75                  80
Ala Val Val Val Ser Ser Glu Cys Ala Arg Glu Cys Phe Thr Glu
                 85                  90                  95
His Asp Val Thr Phe Ala Asn Arg Pro Lys Phe Pro Ser Gln Leu Leu
                100                 105                 110
Val Ser Phe Asn Gly Thr Ala Leu Val Thr Ser Ser Tyr Gly Pro His
            115                 120                 125
Trp Arg Asn Leu Arg Arg Val Ala Thr Val Gln Leu Leu Ser Ala His
130                 135                 140
Arg Val Ala Cys Met Ser Gly Val Ile Ala Ala Glu Val Arg Ala Met
145                 150                 155                 160
Ala Arg Arg Leu Phe His Ala Thr Glu Ala Ser Pro Asp Gly Ala Ala
                165                 170                 175
Arg Val Gln Leu Lys Arg Arg Leu Phe Glu Leu Ser Leu Ser Val Leu
            180                 185                 190
Met Glu Thr Ile Ala Gln Thr Lys Ala Thr Arg Ser Glu Ala Asp Ala
            195                 200                 205
Asp Thr Asp Met Ser Val Glu Ala Gln Glu Phe Lys Glu Val Val Asp
210                 215                 220
Lys Leu Ile Pro His Leu Gly Ala Ala Asn Met Trp Asp Tyr Leu Pro
225                 230                 235                 240
Val Met Arg Trp Phe Asp Val Phe Gly Val Arg Asn Lys Ile Leu His
                245                 250                 255
Ala Val Ser Arg Arg Asp Ala Phe Leu Arg Arg Leu Ile Asp Ala Glu
            260                 265                 270
Arg Arg Arg Leu Ala Asp Gly Gly Ser Asp Gly Asp Lys Lys Ser Met
            275                 280                 285
Ile Ala Val Leu Leu Thr Leu Gln Lys Thr Glu Pro Lys Val Tyr Thr
290                 295                 300
Asp Thr Met Ile Thr Ala Leu Cys Ala Asn Leu Phe Gly Ala Gly Thr
305                 310                 315                 320
Glu Thr Thr Ser Thr Thr Thr Glu Trp Ala Met Ser Leu Leu Leu Asn
                325                 330                 335
His Pro Ala Ala Leu Lys Lys Ala Gln Ala Glu Ile Asp Ala Ser Val
            340                 345                 350
Gly Thr Ser Arg Leu Val Ser Val Asp Asp Val Pro Ser Leu Ala Tyr
            355                 360                 365
Leu Gln Cys Ile Val Ser Glu Thr Leu Arg Leu Tyr Pro Ala Ala Pro
370                 375                 380
Leu Leu Leu Pro His Glu Ser Ser Ala Asp Cys Lys Val Gly Gly Tyr
385                 390                 395                 400
Asn Val Pro Ala Asp Thr Met Leu Ile Val Asn Ala Tyr Ala Ile His
                405                 410                 415
Arg Asp Pro Ala Ala Trp Glu Asp Pro Leu Glu Phe Arg Pro Glu Arg
            420                 425                 430
Phe Glu Asp Gly Lys Ala Glu Gly Leu Phe Met Ile Pro Phe Gly Met
            435                 440                 445
```

```
Gly Arg Arg Cys Pro Gly Glu Thr Leu Ala Leu Arg Thr Ile Gly
    450                 455                 460

Met Val Leu Ala Thr Leu Val Gln Cys Phe Asp Trp Glu Pro Val Asp
465                 470                 475                 480

Gly Val Lys Val Asp Met Thr Glu Gly Gly Phe Thr Ile Pro Lys
                485                 490                 495

Ala Val Pro Leu Glu Ala Val Cys Arg Pro Arg Ala Val Met Arg Asp
                500                 505                 510

Val Leu Gln Asn Leu
        515

<210> SEQ ID NO 10
<211> LENGTH: 513
<212> TYPE: PRT
<213> ORGANISM: Zea mays

<400> SEQUENCE: 10

Met Asp Lys Ala Tyr Val Ala Val Leu Ser Val Ala Phe Leu Phe Leu
1               5                   10                  15

Val His Tyr Leu Val Gly Arg Ala Ala Ala Gly Gly Gly Lys Gly Arg
            20                  25                  30

Lys Arg Leu Pro Pro Ser Pro Leu Ala Ile Pro Phe Leu Gly His Leu
        35                  40                  45

His Leu Val Lys Thr Pro Phe His Ser Ala Leu Gly Arg Leu Ala Glu
    50                  55                  60

Arg His Gly Pro Val Phe Ser Leu Arg Met Gly Cys Arg Arg Ala Val
65                  70                  75                  80

Val Val Ser Ser Pro Glu Cys Ala Arg Ala Cys Phe Thr Glu His Asp
                85                  90                  95

Gln Ser Phe Ala Asn Arg Pro Arg Phe Glu Ser Met Arg Leu Val Ser
            100                 105                 110

Phe Asp Gly Ala Met Leu Ser Val Ser Ser Tyr Gly Pro Tyr Trp Arg
        115                 120                 125

Thr Leu Arg Arg Val Ala Ala Val Gln Leu Leu Ser Ala His Arg Val
    130                 135                 140

Ala Cys Met Ser Pro Val Ile Cys Ala Glu Val Arg Ala Met Val Arg
145                 150                 155                 160

Arg Met Ala Arg Leu Ala Ala Gly Gly Ala Ala Arg Val Gln Leu Arg
                165                 170                 175

Arg Arg Leu Phe Glu Leu Ser Leu Gly Val Leu Met Glu Thr Ile Ala
            180                 185                 190

Arg Thr Lys Thr Ser Arg Ser Glu Ala Cys Ala Ala Asp Thr Asp Val
        195                 200                 205

Ser Pro Glu Ala Ser Glu Leu Thr Arg Ile Ser Glu Glu Ile Met Pro
    210                 215                 220

Tyr Leu Gly Thr Ala Asn Leu Trp Asp Tyr Leu Pro Phe Leu Arg Trp
225                 230                 235                 240

Phe Asp Val Phe Gly Val Arg Lys Lys Leu Met Ala Ala Val Arg Trp
                245                 250                 255

Arg Asp Ala Phe Leu Arg Arg Leu Ile Asp Ala Glu Arg Arg Met
            260                 265                 270

Asp Gly Asp Gly Asp Gly Glu Lys Lys Ser Met Ile Ala Val Leu Leu
        275                 280                 285

Ser Leu Gln Lys Ser Glu Pro Glu Leu Tyr Thr Glu Thr Met Ile Met
    290                 295                 300
```

```
Ala Leu Cys Gly Asp Leu Phe Gly Ala Gly Thr Glu Thr Ser Val
305                 310                 315                 320

Thr Thr Glu Trp Ala Met Ser Leu Leu Leu Asn His Pro Glu Ala Leu
            325                 330                 335

Lys Lys Ala Gln Ala Glu Ile Asp Ala Val Val Gly Asn Ser Arg Arg
            340                 345                 350

Leu Ile Thr Ala Asp Asp Val Pro Arg Leu Gly Tyr Leu His Cys Val
            355                 360                 365

Ile Asn Glu Thr Leu Arg Met Tyr Pro Ala Ala Pro Leu Leu Leu Pro
370                 375                 380

His Glu Ser Ala Ala Asp Cys Lys Val Gly Gly Tyr Asp Val Pro Arg
385                 390                 395                 400

Gly Thr Leu Leu Ile Val Asn Ala Tyr Ala Ile His Arg Asp Pro Ala
            405                 410                 415

Val Trp Glu Asp Pro Gly Arg Phe Val Pro Glu Arg Phe Glu Asp Gly
            420                 425                 430

Lys Ala Glu Gly Arg Leu Leu Met Pro Phe Gly Met Gly Arg Arg Lys
            435                 440                 445

Cys Pro Gly Glu Thr Leu Ala Leu Arg Thr Val Gly Leu Val Leu Ala
450                 455                 460

Thr Leu Leu Gln Cys Phe Asp Trp Asp Thr Val Asp Gly Ala Gln Val
465                 470                 475                 480

Asp Met Thr Glu Ser Gly Gly Leu Thr Met Pro Arg Ala Val Pro Leu
            485                 490                 495

Glu Ala Met Cys Lys Pro Arg Ala Ala Met Cys Asp Val Leu Arg Glu
            500                 505                 510

Leu

<210> SEQ ID NO 11
<211> LENGTH: 513
<212> TYPE: PRT
<213> ORGANISM: Zea mays

<400> SEQUENCE: 11

Met Asp Lys Ala Tyr Val Ala Ala Leu Ser Val Ala Phe Leu Phe Leu
1               5                   10                  15

Val His Tyr Leu Val Gly Arg Ala Ala Ala Gly Gly Gly Lys Gly Arg
            20                  25                  30

Lys Arg Leu Pro Pro Ser Pro Leu Ala Ile Pro Phe Leu Gly His Leu
        35                  40                  45

His Leu Val Lys Thr Pro Phe His Ser Ala Leu Gly Arg Leu Ala Glu
    50                  55                  60

Arg His Gly Pro Val Phe Ser Leu Arg Met Gly Cys Arg Arg Ala Val
65                  70                  75                  80

Val Val Ser Ser Pro Glu Cys Ala Arg Ala Cys Phe Thr Glu His Asp
                85                  90                  95

Met Ser Phe Ala Asn Arg Pro Arg Phe Glu Ser Met Arg Leu Val Ser
            100                 105                 110

Phe Asp Gly Ala Met Leu Ser Val Ser Ser Tyr Gly Pro Tyr Trp Arg
        115                 120                 125

Thr Leu Arg Arg Val Ala Ala Val Gln Leu Leu Ser Ala His Arg Val
    130                 135                 140

Ala Cys Met Ser Pro Val Ile Cys Ala Glu Val Arg Ala Met Val Arg
145                 150                 155                 160
```

```
Arg Met Ala Arg Leu Ala Ala Gly Gly Ala Arg Val Gln Leu Arg
            165                 170                 175
Arg Arg Leu Phe Glu Leu Ser Leu Gly Val Leu Met Glu Thr Ile Ala
        180                 185                 190
Arg Thr Lys Thr Ser Arg Ser Glu Ala Cys Ala Ala Asp Thr Asp Val
        195                 200                 205
Ser Pro Glu Ala Ser Glu Leu Thr Arg Ile Ser Glu Glu Ile Met Pro
210                 215                 220
Tyr Leu Gly Thr Ala Asn Leu Trp Asp Tyr Leu Pro Phe Leu Arg Trp
225                 230                 235                 240
Phe Asp Val Phe Gly Val Arg Asn Lys Leu Met Ala Ala Val Arg Trp
                245                 250                 255
Arg Asp Ala Phe Leu Arg Arg Leu Ile Asp Ala Glu Arg Arg Arg Met
                260                 265                 270
Asp Gly Asp Gly Asp Gly Glu Lys Lys Ser Met Ile Ala Val Leu Leu
                275                 280                 285
Ser Leu Gln Lys Ser Glu Pro Glu Leu Tyr Thr Asp Thr Met Ile Met
        290                 295                 300
Ala Leu Cys Gly Asp Leu Phe Gly Ala Gly Thr Glu Thr Thr Ser Val
305                 310                 315                 320
Thr Thr Glu Trp Ala Met Ser Leu Leu Leu Ser His Pro Glu Ala Leu
                325                 330                 335
Lys Lys Ala Gln Ala Glu Ile Asp Ala Val Val Gly Asn Ser Arg Arg
                340                 345                 350
Leu Ile Thr Ala Asp Asp Val Pro Arg Leu Gly Tyr Leu His Cys Val
        355                 360                 365
Ile Asn Glu Thr Leu Arg Met Tyr Pro Ala Ala Pro Leu Leu Leu Pro
        370                 375                 380
His Glu Ser Ala Ala Asp Cys Lys Val Gly Gly Tyr Asp Val Pro Arg
385                 390                 395                 400
Gly Thr Leu Leu Ile Val Asn Ala Tyr Ala Ile His Arg Asp Pro Ala
                405                 410                 415
Val Trp Glu Asp Pro Gly Ser Phe Leu Pro Glu Arg Phe Glu Asp Gly
                420                 425                 430
Lys Ala Glu Gly Arg Leu Leu Met Pro Phe Gly Met Gly Arg Arg Lys
        435                 440                 445
Cys Pro Gly Glu Thr Leu Ala Leu Arg Thr Val Gly Leu Val Leu Ala
450                 455                 460
Thr Leu Leu Gln Cys Phe Asp Trp Asp Thr Asp Gly Ala Glu Val
465                 470                 475                 480
Asp Met Thr Glu Ser Gly Gly Leu Thr Met Pro Arg Ala Val Pro Leu
                485                 490                 495
Glu Ala Met Cys Lys Pro Arg Ala Ala Met Cys Asp Val Leu Arg Glu
                500                 505                 510
Leu

<210> SEQ ID NO 12
<211> LENGTH: 517
<212> TYPE: PRT
<213> ORGANISM: Zea mays
```

<400> SEQUENCE: 12

```
Met Asp Lys Ala Tyr Ile Ala Ala Leu Ser Ala Ala Leu Phe Leu
 1               5                  10                  15

Leu His Tyr Leu Leu Gly Arg Arg Ala Gly Gly Glu Gly Lys Thr Lys
                 20                  25                  30

Gly Ser Gln Arg Arg Leu Pro Pro Ser Pro Pro Ala Ile Pro Phe Leu
             35                  40                  45

Gly His Leu His Leu Val Lys Ala Pro Phe His Ala Ala Leu Ala Arg
         50                  55                  60

Leu Ala Ala Arg His Gly Pro Val Phe Ser Met Arg Leu Gly Thr Arg
 65                  70                  75                  80

Arg Ala Val Val Val Ser Ser Pro Asp Cys Ala Arg Glu Cys Phe Thr
                 85                  90                  95

Glu His Asp Val Asn Phe Ala Asn Arg Pro Leu Phe Pro Ser Met Arg
                100                 105                 110

Leu Ala Ser Phe Asp Gly Ala Met Leu Ser Val Ser Ser Tyr Gly Pro
            115                 120                 125

Tyr Trp Arg Asn Leu Arg Arg Val Ala Ala Val Gln Leu Leu Ser Ala
130                 135                 140

His Arg Val Ala Cys Met Ala Pro Ala Ile Glu Ala Gln Val Arg Ala
145                 150                 155                 160

Met Val Arg Arg Met Asp Arg Ala Ala Ala Gly Gly Gly Gly Ala
                165                 170                 175

Ala Arg Val Gln Leu Lys Arg Arg Leu Phe Glu Leu Ser Leu Ser Val
            180                 185                 190

Leu Met Glu Thr Ile Ala His Thr Lys Thr Ser Arg Ala Glu Ala Asp
            195                 200                 205

Ala Asp Ser Asp Met Ser Pro Glu Ala His Glu Phe Lys Gln Ile Val
            210                 215                 220

Asp Glu Leu Val Pro Tyr Ile Gly Thr Ala Asn Arg Trp Asp Tyr Leu
225                 230                 235                 240

Pro Val Leu Arg Trp Phe Asp Val Phe Gly Val Arg Asn Lys Ile Leu
                245                 250                 255

Asp Ala Val Gly Arg Arg Asp Ala Phe Leu Arg Arg Leu Ile Asp Gly
            260                 265                 270

Glu Arg Arg Arg Leu Asp Ala Gly Asp Ser Glu Ser Lys Ser Met
            275                 280                 285

Ile Ala Val Leu Leu Thr Leu Gln Lys Ser Glu Pro Glu Val Tyr Thr
            290                 295                 300

Asp Thr Val Ile Thr Ala Leu Cys Ala Asn Leu Phe Gly Ala Gly Thr
305                 310                 315                 320

Glu Thr Thr Ser Thr Thr Thr Glu Trp Ala Met Ser Leu Leu Leu Asn
                325                 330                 335

His Arg Glu Ala Leu Lys Lys Ala Gln Ala Glu Ile Asp Ala Ala Val
            340                 345                 350

Gly Thr Ser Arg Leu Val Thr Ala Asp Asp Val Pro His Leu Thr Tyr
            355                 360                 365

Leu Gln Cys Ile Val Asp Glu Thr Leu Arg Leu His Pro Ala Ala Pro
            370                 375                 380

Leu Leu Leu Pro His Glu Ser Ala Ala Asp Cys Thr Val Gly Gly Tyr
385                 390                 395                 400

Asp Val Pro Arg Gly Thr Met Leu Leu Val Asn Val His Ala Val His
                405                 410                 415
```

```
Arg Asp Pro Ala Val Trp Asp Pro Asp Arg Phe Val Pro Glu Arg
                420                 425                 430

Phe Glu Gly Gly Lys Ala Glu Gly Arg Leu Leu Met Pro Phe Gly Met
        435                 440                 445

Gly Arg Arg Lys Cys Pro Gly Glu Thr Leu Ala Leu Arg Thr Val Gly
        450                 455                 460

Leu Val Leu Gly Thr Leu Leu Gln Cys Phe Asp Trp Asp Thr Val Asp
465                 470                 475                 480

Gly Ala Gln Val Asp Met Lys Ala Ser Gly Gly Leu Thr Met Pro Arg
                485                 490                 495

Ala Val Pro Leu Glu Ala Met Cys Arg Pro Arg Thr Ala Met Arg Asp
                500                 505                 510

Val Leu Lys Arg Leu
        515

<210> SEQ ID NO 13
<211> LENGTH: 513
<212> TYPE: PRT
<213> ORGANISM: Oryza sativa

<400> SEQUENCE: 13

Met Asp Asn Ala Tyr Ile Ile Ala Ile Leu Ser Val Ala Ile Leu Phe
1               5                   10                  15

Leu Leu His Tyr Tyr Leu Leu Gly Arg Gly Asn Gly Gly Ala Ala Arg
                20                  25                  30

Leu Pro Pro Gly Pro Pro Ala Val Pro Ile Leu Gly His Leu His Leu
            35                  40                  45

Val Lys Lys Pro Met His Ala Thr Met Ser Arg Leu Ala Glu Arg Tyr
    50                  55                  60

Gly Pro Val Phe Ser Leu Arg Leu Gly Ser Arg Arg Ala Val Val Val
65                  70                  75                  80

Ser Ser Pro Gly Cys Ala Arg Glu Cys Phe Thr Glu His Asp Val Thr
                85                  90                  95

Phe Ala Asn Arg Pro Arg Phe Glu Ser Gln Leu Leu Val Ser Phe Asn
            100                 105                 110

Gly Ala Ala Leu Ala Thr Ala Ser Tyr Gly Ala His Trp Arg Asn Leu
        115                 120                 125

Arg Arg Ile Val Ala Val Gln Leu Leu Ser Ala His Arg Val Gly Leu
    130                 135                 140

Met Ser Gly Leu Ile Ala Gly Glu Val Arg Ala Met Val Arg Arg Met
145                 150                 155                 160

Tyr Arg Ala Ala Ala Ala Ser Pro Ala Gly Ala Ala Arg Ile Gln Leu
                165                 170                 175

Lys Arg Arg Leu Phe Glu Val Ser Leu Ser Val Leu Met Glu Thr Ile
            180                 185                 190

Ala His Thr Lys Ala Thr Arg Pro Glu Thr Asp Pro Asp Thr Asp Met
        195                 200                 205

Ser Val Glu Ala Gln Glu Phe Lys Gln Val Val Asp Glu Ile Ile Pro
    210                 215                 220

His Ile Gly Ala Ala Asn Leu Trp Asp Tyr Leu Pro Ala Leu Arg Trp
225                 230                 235                 240

Phe Asp Val Phe Gly Val Arg Arg Lys Ile Leu Ala Ala Val Ser Arg
                245                 250                 255

Arg Asp Ala Phe Leu Arg Arg Leu Ile Asp Ala Glu Arg Arg Arg Leu
            260                 265                 270
```

Asp Asp Gly Asp Glu Gly Glu Lys Lys Ser Met Ile Ala Val Leu Leu
            275                 280                 285

Thr Leu Gln Lys Thr Glu Pro Glu Val Tyr Thr Asp Asn Met Ile Thr
290                 295                 300

Ala Leu Thr Ala Asn Leu Phe Gly Ala Gly Thr Glu Thr Thr Ser Thr
305                 310                 315                 320

Thr Ser Glu Trp Ala Met Ser Leu Leu Leu Asn His Pro Asp Thr Leu
                325                 330                 335

Lys Lys Ala Gln Ala Glu Ile Asp Ala Ser Val Gly Asn Ser Arg Leu
            340                 345                 350

Ile Thr Ala Asp Val Thr Arg Leu Gly Tyr Leu Gln Cys Ile Val
            355                 360                 365

Arg Glu Thr Leu Arg Leu Tyr Pro Ala Ala Pro Met Leu Leu Pro His
370                 375                 380

Glu Ser Ser Ala Asp Cys Lys Val Gly Gly Tyr Asn Ile Pro Arg Gly
385                 390                 395                 400

Ser Met Leu Leu Ile Asn Ala Tyr Ala Ile His Arg Asp Pro Ala Val
                405                 410                 415

Trp Glu Glu Pro Glu Lys Phe Met Pro Glu Arg Phe Glu Asp Gly Gly
            420                 425                 430

Cys Asp Gly Asn Leu Leu Met Pro Phe Gly Met Gly Arg Arg Arg Cys
            435                 440                 445

Pro Gly Glu Thr Leu Ala Leu Arg Thr Val Gly Leu Val Leu Gly Thr
            450                 455                 460

Leu Ile Gln Cys Phe Asp Trp Glu Arg Val Asp Gly Val Glu Val Asp
465                 470                 475                 480

Met Thr Glu Gly Gly Gly Leu Thr Ile Pro Lys Val Val Pro Leu Glu
                485                 490                 495

Ala Met Cys Arg Pro Arg Asp Ala Met Gly Gly Val Leu Arg Glu Leu
            500                 505                 510
Val

<210> SEQ ID NO 14
<211> LENGTH: 520
<212> TYPE: PRT
<213> ORGANISM: Zea mays

<400> SEQUENCE: 14

Met Asp Lys Ala Tyr Val Ala Val Leu Ser Phe Ala Phe Leu Phe Val
1               5                   10                  15

Ile His Tyr Leu Val Gly Arg Ala Gly Arg Lys Gly Asn Gly Lys Gly
            20                  25                  30

Lys Gly Thr Gln Arg Leu Pro Pro Ser Pro Ala Val Pro Phe Leu
            35                  40                  45

Gly His Leu His Leu Val Lys Thr Pro Phe His Glu Ala Leu Ala Gly
        50                  55                  60

Leu Ala Ala Arg His Gly Pro Val Phe Ser Met Arg Met Gly Ser Arg
65                  70                  75                  80

Arg Ala Leu Val Val Ser Ser Pro Glu Cys Ala Lys Glu Cys Phe Thr
                85                  90                  95

Glu His Asp Val Val Phe Ala Asn Arg Pro Arg Phe Ala Thr Gln Asp
            100                 105                 110

Leu Val Ser Phe Gly Gly Ala Ala Leu Ala Ala Ala Ser Tyr Gly Pro
        115                 120                 125

```
Tyr Trp Arg Asn Leu Arg Arg Val Ala Thr Val Gln Leu Leu Ser Ala
    130                 135                 140

His Arg Val Ala Cys Met Ser Ala Val Val Ala Ala Glu Val Arg Ala
145                 150                 155                 160

Met Ala Arg Arg Met Gly Arg Ala Ala Ala Ala Pro Gly Gly Ala
                165                 170                 175

Ala Arg Val Gln Leu Lys Arg Arg Leu Phe Glu Val Ser Leu Ser Val
                180                 185                 190

Leu Met Glu Thr Ile Ala Arg Thr Lys Thr Ser Arg Ala Glu Ala Asp
            195                 200                 205

Ala Asp Ser Asp Met Ser Pro Glu Ala His Glu Phe Lys Gln Ile Val
210                 215                 220

Asp Glu Ile Val Pro His Leu Gly Thr Ala Asn Leu Trp Asp Tyr Leu
225                 230                 235                 240

Pro Val Leu Arg Trp Leu Asp Val Phe Gly Val Arg Asn Lys Ile Thr
                245                 250                 255

Ala Ala Val Gly Arg Arg Asp Ala Phe Leu Arg Arg Leu Ile Asp Ala
                260                 265                 270

Glu Arg Arg Arg Leu Asp Asp Gly Gly Asp Ser Asp Ser Asp Lys
            275                 280                 285

Lys Ser Met Ile Ala Val Leu Leu Ser Leu Gln Lys Ser Glu Pro Glu
290                 295                 300

Val Tyr Thr Asp Thr Met Ile Met Ala Leu Cys Gly Asn Leu Phe Gly
305                 310                 315                 320

Ala Gly Thr Glu Thr Thr Ser Thr Thr Thr Glu Trp Ala Met Ser Leu
                325                 330                 335

Leu Leu Asn His Pro Glu Ala Leu Lys Lys Ala Gln Ala Glu Ile Asp
            340                 345                 350

Ala Val Val Gly Thr Ser Arg Leu Leu Ala Ala Glu Asp Val Pro Arg
            355                 360                 365

Leu Gly Tyr Leu His Arg Val Ile Ser Glu Thr Leu Arg Met Tyr Pro
370                 375                 380

Ala Ala Pro Leu Leu Leu Pro His Glu Ser Ser Ala Asp Cys Lys Val
385                 390                 395                 400

Gly Gly Tyr Asp Val Ala Arg Gly Thr Leu Leu Ile Val Asn Ala Tyr
                405                 410                 415

Ala Ile His Arg Asp Pro Leu Val Trp Glu Asp Pro Asp Glu Phe Arg
            420                 425                 430

Pro Glu Arg Phe Glu Asp Gly Lys Ala Glu Gly Arg Leu Leu Met Pro
            435                 440                 445

Phe Gly Met Gly Arg Arg Lys Cys Pro Gly Glu Thr Leu Ala Leu Arg
450                 455                 460

Thr Ile Ser Leu Val Leu Gly Thr Leu Ile Gln Cys Phe Asp Trp Asp
465                 470                 475                 480

Arg Val Asp Gly Leu Glu Ile Asp Met Ala Ala Gly Gly Gly Leu Thr
                485                 490                 495

Leu Pro Arg Ala Val Pro Leu Glu Ala Thr Cys Lys Pro Arg Ala Ala
            500                 505                 510

Val Arg His Leu Leu Leu Glu Leu
            515                 520
```

<210> SEQ ID NO 15
<211> LENGTH: 1700
<212> TYPE: DNA
<213> ORGANISM: Artificial Sequence
<220> FEATURE:
<223> OTHER INFORMATION: Synthesized
<220> FEATURE:
<223> OTHER INFORMATION: Glyphosate-resistant EPSPS gene

<400> SEQUENCE: 15

```
ctcgagtcaa cacaacatat acaaaacaaa cgaatctcaa gcaatcaagc attctacttc      60
tattgcagca atttaaatca tttcttttaa agcaaaagca attttctgaa aattttcacc     120
atttacgaac gatagccatg gctcaagtta gcagaatctg caatggtgtg cagaacccat     180
ctcttatctc caatctctct aaatccagtc aaaggaaatc tcccttatcg gtttctctga     240
agactcagca gcatccacga gcttatccaa tttcttcatc gtggggattg aagaagagtg     300
ggatgacttt aattggctct gagcttcgtc tcttaaggt catgtcttct gtttccacgg      360
cggagaaggg atccgacgct cttccagcta ccttcgacgt tatcgtgcat ccagctagag     420
aactcagagg tgaacttaga gcacagccat ccaagaacta caccactaga tacctcctcg     480
ccgctgctct cgctgagggt gaaaccagag ttgttggtgt ggctacctct gaggatgccg     540
aagctatgct cagatgcctc agagattggg gtgctggtgt tgagcttgtt ggtgatgacg     600
ccgtgatcag aggtttcggt gctagaccac aggctggtgt taccccttaac ccaggtaacg     660 ctggtgcagt ggccagattc cttatgggtg ttgctgctct caccttctggt acaactttcg     720 ttaccgatta ccctgattcc cttggtaaga gacctcaggg tgaccttctt gaagccctcg     780
aaagacttgg tgcttgggtg tcctccaacg atggtagact ccctatctcc gtttccggtc     840
cagttagagg tggtacagtg gaggttccg ccgaaagatc ctcccagtac gcttccgccc      900
ttatgttcct cggtcctctt cttcctgacg gactcgaact tagactcacc ggtgatatca     960
agtcccacgc tcctcttaga cagacacttg acaccctctc tgatttcggt gttagagcta    1020
ctgcctccga tgaccttaga agaatctcca tccctggtgg tcagaagtac agaccaggta    1080
gagtgctcgt tcctggtgat taccctggtt ccgctgctat ccttaccgcc gctgctcttc    1140
tcccaggtga ggttagactt tctaacctta gagaacacga cctccagggt gagaaggaag    1200
ctgtgaacgt tcttagagag atgggtgctg atatcgttag agaaggtgat acccttaccg    1260
tgagaggtgg tagacctctc cacgctgtta ctagagatgg tgattccttc accgacgccg    1320
tgcaagctct taccgctgct gctgccttcg ctgagggtga taccaccctgg gaaaacgttg    1380 ctactcttag actcaaggaa tgcgatagaa tctctgacac cagagctgag cttgaaagac    1440
ttggtcttag agcaagagag accgccgatt ctctctccgt tactggttct gctcaccttg    1500
ctggtggtat caccgctgat ggtcacggtg accacagaat gatcatgctt ctcacccttc    1560
ttggtctcag agcagatgct ccacttagaa tcaccggtgc acaccacatc agaaagtcct    1620
accctcagtt cttcgctcac cttgaagctc ttggtgctag attcgaatac gctgaggcta    1680
ccgcctaata ggagctcgag                                                1700
```

<210> SEQ ID NO 16
<211> LENGTH: 28
<212> TYPE: DNA
<213> ORGANISM: Artificial Sequence
<220> FEATURE:
<223> OTHER INFORMATION: Synthesized

```
<400> SEQUENCE: 16
acggcccgca ctggcgcaac ctccgccg                                           28

<210> SEQ ID NO 17
<211> LENGTH: 30
<212> TYPE: DNA
<213> ORGANISM: Artificial Sequence
<220> FEATURE:
<223> OTHER INFORMATION: Synthesized

<400> SEQUENCE: 17
gttcctcacg ccgaacacgt cgaaccaccg                                         30

<210> SEQ ID NO 18
<211> LENGTH: 42
<212> TYPE: DNA
<213> ORGANISM: Artificial Sequence
<220> FEATURE:
<223> OTHER INFORMATION: Synthesized

<400> SEQUENCE: 18
gcgaagcttg catgcctaca gtgcagcgtg acccggtcgt gc                           42

<210> SEQ ID NO 19
<211> LENGTH: 46
<212> TYPE: DNA
<213> ORGANISM: Artificial Sequence
<220> FEATURE:
<223> OTHER INFORMATION: Synthesized

<400> SEQUENCE: 19
gtgggatcct ctagagtcga cctgcagaag taacaccaaa caacag                       46
```

HERBICIDE RESISTANCE GENE AND USE THEREOF

CROSS-REFERENCE TO RELATED APPLICATIONS

This application is the U.S. National Stage of International Application PCT/CN2011/082312 filed Nov. 16, 2011, which designates the U.S and was published by the International Bureau in Chinese on May 13, 2012, and which claims the benefit of Chinese Application No. 201010556653.X, filed Nov. 22, 2010, both of which are hereby incorporated by reference in their entirety.

TECHNICAL FIELD

The present invention belongs to the field of plant genetic engineering, specifically, the present invention relates to genes and encoded proteins thereof resistant to a variety of herbicides such as nicosulfuron, mesotrione, and 2,4D. Such genes can be used to be expressed in a plant to enhance the resistance of the plant to herbicides. The present invention can be applied in the fields such as plant breeding and screening of plant cell culture.

BACKGROUND ART

There is a need to prevent and control weeds in crop planting process. If a crop is capable of obtaining resistance capability to broad-spectrum herbicides, the weeds of such crop can be prevented and controlled by spraying broad-spectrum herbicides after the seedling emergence. Such prevention and control method for weeds is simple, highly efficient, low in cost, and safe to crops.

Crops can acquire resistance to a herbicide through genetic engineering improvement. For example, crops can obtain glyphosate resistance capability through transgenic expression of 5-enolpyruvylshikimate-3-phosphate synthase (EPSPS) of Agrobacterium (Agrobacterium tumefaciens sp CP4). Transgenic glyphosate-resistant plants expressing such enzymes have been applied in production (U.S. Pat. Nos. 453,590, 4,769,061, 5,094,945). In order to control the occurrence of herbicide resistance of weeds, to improve the resistance level of the transgenic crops and to increase the diversity of the resistance genes, it is very useful to develop resistant transgenic crops in production which are resistant to other herbicides than glyphosate.

Cytochrome P450 is a large gene family. Usually, there are more than 200 P450 genes in a plant. It is found in prior study that part of the P450 genes are genes capable of degrading herbicides. For instance, a hybridized molecule of a cytochrome P450 gene P4507A1 of an animal and a NADPH-cytochrome P450 gene of a yeast can be resistant to a herbicide. (Shiota et al. 1994 Plant Physiol. 106: 17). CYP71A10 is a cytochrome P450 gene isolated from soybean, and the resistance of transgenic tobacco to Linuron and chlortoluron can be improved by expressing such gene in tobacco. (Siminszky et al., 1999 Proc Natl Acad Sci USA 96: 1750-1755; Siminszky et al, 2000, Weed Sci 48:291-295). A cytochrome P450 gene (having a polynucleotide sequence of SEQ ID: 5 and an amino acid sequence of SEQ ID: 6) in maize is found to have the capability of resistance to herbicides such as nicosulfuron (Chinese patent, application number 200610155661; and US patent US 20080052798 A1). A cytochrome P450 gene in rice also has resistance to Bentazon and sulfonylurea herbicides (Pan et al., Plant Molecular Biology, 2006, 61: 933-943). Other cytochrome P450 genes from different sources also have the function of resisting herbicides and can be used to obtain transgenic plants resistant to herbicide. For instance, Didierjean et al. (2002) Plant Physiol. 130: 179-189; Morant et al. (2003) Opinion in Biotechnology 14:151-162.

The present invention provides genes resistant to several highly efficient herbicides and a method for obtaining transgenic herbicide-resistant plants using the genes.

CONTENTS OF THE INVENTION

The problem to be solved in the present invention is to provide a gene having herbicide resistance performance.

*Cynodon dactylon* is a plant tolerant to herbicides such as nicosulfuron and mesotrione. Thus it is hopeful to clone genes resistant to herbicides from this plant and apply such genes to breed herbicide-resistant transgenic crops. The present invention clones a gene from *Cynodon dactylon*, which obviously resists multiple herbicides. These herbicides belong to acetolactate synthase (ALS)-inhibiting herbicides, protoporphyrinogen oxidase (PPO)-inhibiting herbicides, p-hydroxyphenylpyruvate dioxygenase (HPPD)-inhibiting herbicides, photosystem II-inhibiting herbicides, and synthetic auxin herbicides, respectively. The present invention provides this gene and a method for obtaining transgenic herbicide-resistant crops using such gene.

The present invention is described in detail as follows:

The present invention provides a gene having herbicide resistance performance. The protein encoded by the polynucleotide sequence of such gene is SEQ ID NO: 1, or has at least 80%, 85%, 90% or 95% amino acid sequence identity as compared to SEQ ID NO:1. The amino acid identity can be obtained by existing method. For example, Karlin and Altschul (1990) Proc. Natl. Acad. Sci. USA 87: 3364; and Karlin and Altschul (1993) Proc. Natl. Acad. Sci. USA 90:5873-5877. The gene is characterized in that the expression of the protein polypeptide encoded by this gene in the plants can result in improved resistance to one or more herbicides belonging to the following type(s) of herbicides: 1) acetolactate synthase (ALS)-inhibiting herbicides, including but not limited to sulfonylurea herbicides, imidazolinone herbicides, triazole pyrimidine sulfonamide herbicides, and salicylic acid pyrimidine herbicides. Among others, the commonly used herbicides include nicosulfuron, rimsulfuron, chlorsulfuron, and penoxsulam, etc; 2) protoporphyrinogen oxidase (PPO)-inhibiting herbicides, including but not limited to diphenyl ether, fluoroglycofen, oxyfluorfen, fomesafen, flumioxazin, flumiclorac-pentyl, acifluorfen, etc; 3) p-hydroxyphenylpyruvate dioxygenase (HPPD)-inhibiting herbicides, including but not limited to mesotrione, mesotrione, isoxazolone, etc; 4) photosystem II-inhibiting herbicides, including but not limited to atrazine, paraquat, bentazon and bromoxynil; and 5) synthetic auxin herbicides, including but not limited to 2,4-D butylate (2,4D) and dicamba, etc.

There are many cytochrome P450 genes in plants. For example, it is estimated that there are more than 300 cytochrome P450 genes in the genome of *Arabidopsis thaliana* (Werck-Reichhart et al., Trends in Plant Science 5: 116-123). The amino acid sequences of the herbicide resistance genes provided in the present invention have different degrees of identity to a series of cytochrome P450 genes which have been known. For example, the following cytochrome P450 genes in the genebank are found to have relatively high identity to the amino acid sequences of the genes provided by the present invention:

1) Maize (*Zea mays*) ACG28028.1 (SEQ ID No:6), 76% identity;
2) Sorghum (Sorghum bicolor) gene XP_002466416 (SEQ ID No:7), 79% identity;
3) Barley (*Hordeum vulgare*) BAJ94385.1 (SEQ ID No:8), 75% identity;
4) Ryegrass (*Hordeum vulgare*) AAK3 8080.1 (SEQ ID No:9), 73% identity;
5) Maize (*Zea mays*) ACG29853.1 (SEQ ID No: 10), 74% identity;
6) Maize (*Zea mays*) NP_001142304 (SEQ ID No: 11), 74% identity;
7) Maize (*Zea mays*) ACG27785 (SEQ ID No: 12), 77% identity;
8) Rice (*Oryza sativa*) ABC69856.1 (SEQ ID No: 13), 73% identity;
9) Maize (*Zea mays*) 2m-513 (SEQ ID No: 14), 79% identity.

These genes have relatively high identity and they may be homologous in evolution. According to the identity of the amino acid sequences, their relationships in evolution are shown as FIG. 1. However, up to now whether the cytochrome p450 gene in a plant has herbicide resistance capability can not be predicted accurately. For example, a cytochrome p450 gene Zm-513 (amino acid sequence being SEQ ID NO:14) in maize genome which is very similar to a gene provided in present invention does not have herbicide resistance capability. Likewise, another highly homologous cytochrome p450 gene N-Z2 (amino acid sequence SEQ ID No: 3) cloned and obtained from *Cynodon dactylon* does not exhibit herbicide resistance capability either (example 5). Accordingly, the herbicide resistance capability of the herbicide resistance gene N-Z1 disclosed in the present invention cannot be predicted according to its sequence and the identity of the herbicide resistance genes which have been known.

The present invention also includes herbicide resistance genes obtained via gene recombinant technology using the polynucleotide fragment of the encoded protein polypeptide SEQ ID NO:1. For example, new recombinant genes can be obtained from 2 or more homogenous genes by DNA shuffling method (US 2002/0058249; Stemmer (1994) Proc. Natl. Acad. Sci. USA 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) Proc. Natl. Acad. Sci. USA 94:4504-4509; Crameri et al. (1998) Nature 391:288-291; and U.S. Pat. Nos. 5,605,793 and 5,837,458). A person of ordinary skill in the art can obtain variants which still have the same herbicide resistance activity or changed herbicide resistance performance. In addition, the polypeptide having approximately 100-120 amino acids at the N-terminal of the herbicide resistance polypeptide provided in the present invention is a signal peptide introduced into chloroplasts. This signal peptide usually can be replaced by other chloroplast signal peptides without affecting the herbicide resistance function of the protein.

The polynucleotides and the variants of the encoded proteins thereof provided in the present invention also constitute the part of the present invention to be protected. The variants refer to polynucleotides or proteins with highly similar sequences. The variants of the polynucleotide sequences include polynucleotides in which deletion, insertion or substitution take places at one or more sites, and these variations remain do not change the open reading expression cassette and maintain their herbicide resistance capability. The sources of the variations of a polynucleotide may be from multiple aspects. One situation is that codons encoding the same amino acid are different, i.e. the polynucleotide sequences encoding the same amino acid sequence may be different; the other situation is the natural diversity existed in different individuals in organisms or related species; and further situation is variations introduced via artificial means. Currently there are many methods for manually introducing variations, which can be obtained by a person of ordinary skill in the art through existing technologies, for example, Kunkel (1985) Proc. Natl. Acad. Sci. USA 82:488-492; Kunkel et al. (1987) Methods in Enzymol. 154:367-382; U.S. Pat. No. 4,873,192; and Walker and Gaastra, eds. (1983) Techniques in Molecular Biology (MacMillan Publishing Company, New York.

The variants of protein polypeptides include variant proteins in which one or more amino acids is deleted, inserted or substituted at one or more sites. The variants for protection in the present invention are proteins that still retain the herbicide resistance activity of their natural genes, i.e. can result in the herbicide resistance activity of the transgenic plant. Such variants can be derived from genetic polymorphism of organisms or by variation via artificial genetic manipulation. Artifical genetic manipulation can realize the substitution, deletion or insertion of amino acids of proteins. These genetic manipulation methods are known and can be implemented by a person of ordinary skill in the art. The deletion, substitution or insertion variations of protein sequences in many cases will not obviously change the biological activity of the protein. Even though the effects of these variations on the activity of the protein cannot be predicted, a person of ordinary skill in the art can make the proteins encoded by these variants express in plants to evaluate their herbicide resistance capabilities.

The polynucleotides provided by the present invention can also be used to clone corresponding genes from other plants. According to the polynucleotide sequences provided by the present invention, a person of ordinary skill in the art can clone corresponding homologous genes form a plant by PCR method and DNA hybridization method. For the PCR method, primers can be designed according to the polynucleotide sequences provided by the present invention, especially according to the sequences of the conserved regions, and the sequences of part or all of the homologous genes can be obtained via PCR method. For the DNA hybridization method, probes can be prepared using the polynucleotides provided by the present invention, and the homogenous genes can be obtained by hybridizing with DNA library. Moreover, a person of ordinary skill in the art can search out the genes with high homology from a genomic library using the nucleic acid sequences and protein sequences provided by the present invention by molecular bioinformatics method. For example, genes having relatively high homology with the genes provided by the present invention can be found out using BLAST (www.ncbi.nih. gov) method according to the polynucleotide sequences and the amino acid sequences of the encoded protein polypeptides thereof provided by the present invention. Usually, the protein whose amino acid sequence of the protein polypeptide has at least 80%, 85%, 90%, 95% or 99% identity to the herbicide resistance gene of the present invention may have herbicide resistance activity, and can be determined and validated by the methods which have existed. Accordingly, the herbicide resistance genes of the present invention encompass these homologous genes.

The present invention, using the herbicide resistance genes, provides a method for obtaining transgenic plants capable of resisting herbicides. Such a herbicide-resistant transgenic plant can avoid the damage of herbicide to the plant, and provides a convenient and economic way for selectively kill weeds. The method for obtaining transgenic herbicide-resistant plant provided by the present invention comprises: 1) constructing an expression cassette which can express the herbicide resistance gene of the present invention, i.e. functionally linking the polynucleotide sequence capable of controlling expression to the herbicide resistance gene; 2) introducing the polynucleotide expression cassette capable of expressing the herbicide resistance protein polypeptide provided in the present invention into the plant cells; 3) breeding the transformed plant cells into transgenic plants; and 4) selecting the transgenic plants having herbicide resistance capability. A person of ordinary skill in the art can construct herbicide resistance gene expression cassette and transform the plants according to known knowledge and using the polynucleotide sequence provided by the present invention, so as to obtain herbicide-resistant transgenic plants. Herbicide-resistant transgenic plants are transgenic plants having improved resistance to herbicides as compared to non-transgenic parental plants. The transgenic plants obtained by the present invention has the resistance to at least one of the following types of herbicides: acetolactate synthase (ALS)-inhibiting herbicides, protoporphyrinogen oxidase (PPO)-inhibiting herbicides, p-hydroxyphenylpyruvate dioxygenase (HPPD)-inhibiting herbicides, photosystem II-inhibiting herbicides, and synthetic auxin herbicides. These types of herbicides include but not limited to nicosulfuron, mesotrione, dicamba, and 2,4-D butylate (2,4D), etc.

The expression of the herbicide resistance polypeptide encoded by the polynucleotide can be realized by constructing an expression cassette of the herbicide resistance gene. The expression cassette is obtained by functionally linking one or more polynucleotide sequences that control expression to the polynucleotide sequences resistant to herbicides. Usually, the expression cassette of the herbicide resistance gene is constructed on a plasmid vector. The vector can acquire a large quantity of replications in cells. The expression regulation sequence of the expression cassette usually comprises a promoter and a terminator. The promoter is usually linked at the 5' end, while the terminator is linked at the 3' end. Said functional link means that the promoter and the terminator can play the role of starting and controlling the expression of polynucleotide linked thereto.

The control of gene expression promoter is a technology known to those skilled in the art. Studies concerning the promoters are introduced and summarized in detail in a review of Potenza et. al. (Potenza et al. (2004) In Vitro Cell Dev Biol-Plant 40:1-22). Promoter includes constitutive expression promoter, tissue-specific expression promoter, and inducible expression promoter. The natural promoter of the gene provided in the present invention can also be used to control the expression of herbicide resistance gene. However, the constitutive expression promoter is widely used for controlling the herbicide resistance gene. Constitutive promoter is a promoter that can be expressed during the whole growth and development period of various plant tissues. For example, CaMV 35S promoter (Odell et al. 1985 Nature 313:810-812); rice actin promoter (McElroy et al. 1990 Plant Cell 2:163-171); and maize ubiquitin promoter (Christensen et al. 1989 Plant Mol. Biol. 12:619-632 and Christensen et al. 1992 Plant Mol. Biol. 18:675-689). All of these promoters can be used to control the genes provided in the present invention to express in plants, so as to obtain the transgenic herbicide-resistant plants.

The terminator that controls the expression of the genes may be a natural terminator of the provided gene, or a terminator derived from other genes of the plants, or a polynucleotide fragment having the function of the terminator in other plants. The commonly used terminators include octopine synthase terminator and nopaline synthase terminator derived from *Agrobacterium*, and 35S gene terminator of CaMV plant virus. References include: Guerineau et al. (1991) Mol. Gen. Genet 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; and Joshi et al. (1987) Nucleic Acids Res. 15:9627-9639.

The polynucleotide sequence of the gene can be further modified and altered in order to provide the expression level of the gene in the target plant. Such alterations include deleting introns, and removing some sequences that may affect the normal expression, such as immature Poly A signal sequences, etc. Polynucleotide sequences that encode the same protein polypeptide can be optimized according to the codon usage of the target plant to improve the expression in the target plant. Translation enhancing sequences can also be added to the non-coding region sequence at the 5'end when constructing the gene expression cassette. For example, enhancing sequences of picornavirus; and TEV (Tobacco Etch Virus) enhancing sequences (Gallie et al. 1995 Gene 165:233-238), etc.

The vector of the expression cassette of the gene provided in the present invention can also comprises a selective marker gene expression cassette at the same time. The selective marker gene can be used to select the transformed cells. The commonly used selective marker gene includes antibiotic resistance genes, such as hygromycin resistance gene (HPT), glyphosate resistance gene and glufosinate resistance gene. Other selective marker genes can also be used as the selective gene for transformation of the present invention.

The genes provided in the present invention can be introduced into the plants to obtain the transgenic herbicide-resistant plants, such plants include but not limited to maize, wheat, barley, sorghum, rice, soybean, carrot, potato, cotton, sunflower, rape, oak tree, turfgrass, and pasturage.

Transgenic methods for plants are comparatively mature at present. The polynucleotides provided in the present invention can be introduced into a variety of plants by a person of ordinary skill in the art using the technologies which have existed. The commonly used methods include gene gun method (Klein et al, 1987, Nature (London) 327:70-73; U.S. Pat. No. 4,945,050) or *Agrobacterium tumefaciens* mediated method (De Blaere et al, 1987, Meth. Enzymol. 143:277). However, the present invention is not limited to these methods.

The transformation methods and steps are somewhat different for different plants. However, immature embryos, mature embryos, undifferentiated calli or protoplasts of plants are commonly introduced via *Agrobacterium* or gene gun. Then the cultures are screened using corresponding screening media. Then, transformed buds are obtained through differentiation and plantable transgenic seedlings can be obtained through culturing via rooting medium. Further, the herbicide-resistant transgenic plants can be screened by spraying herbicides, for example, the non-transgenic rice can be killed by spraying nicosulfuron. The plants involved in the present invention include but not limited to maize, wheat, barley, sorghum, rice, soybean, carrot, potato, cotton, sunflower, rape, oak tree, turfgrass and forage grass.

DESCRIPTION OF FIGURES

The particular example of the present invention will be further described hereinbelow in conjunction with the accompanying drawings.

FIG. 1: Identity analysis of amino acid sequences for part of the known cytochrome P450 genes The evolution relationship diagram is obtained using the procedures of Vector NT (7.0).N-Z1: a cytochrome P450 gene isolated from *Cynodon dactylon* (amino acid sequence being SEQ ID NO:1); N-Z2: another cytochrome P450 gene isolated from *Cynodon dactylon* (amino acid sequence being SEQ ID NO:3); AAK38080: genebank number of cytochrome P450 gene of ryegrass (*Lolium rididum*) (amino acid sequence being SEQ ID NO: 9); BAJ94385: genebank number of cytochrome P450 gene of barley (*Hordeum vulgare*) (amino acid sequence being SEQ ID NO:8); ABC69856.1: genebank number of cytochrome P450 gene of rice (amino acid sequence being SEQ ID NO:13), this gene is found to be resistant to Bentazon and sulfonylurea herbicides; ACG27785: genebank number of cytochrome P450 gene of maize (amino acid sequence being SEQ ID NO:12); ACG28028: genebank number of cytochrome P450 gene of maize (amino acid sequence being SEQ ID NO: 6), with a gene name of CYP81A9, having herbicide resistance function; ACG29853: genebank number of cytochrome P450 gene of maize (amino acid sequence is SEQ ID NO: 10), with a gene name of CYP81A3v2; NP_001142304: genebank number of cytochrome P450 gene of maize (amino acid sequence being SEQ ID NO: 11); XP_002466416: genebank number of cytochrome P450 gene of sorghum (amino acid sequence being SEQ ID NO: 7); and Zm-513: genebank number of cytochrome P450 gene of maize (amino acid sequence being SEQ ID NO: 14), without finding herbicide resistance capability.

PARTICULAR EMBODIMENTS

The present invention will be further described hereinbelow in conjunction with the particular examples, but the scope of protection for the present invention is not limited thereto.

All of the molecular biological and biochemical methods used in the following examples of the present invention are known technologies. They are described in detail in references such as Current Protocols in Molecular Biology, edited by Ausubel, published by John Wiley and Sons company, and Molecular Cloning: A Laboratory Manual, 3rd ED, edited by J. Sambrook et al, published by Cold Spring Harbor Laboratory Press (2001).

EXAMPLE 1

Resistance Determination of *Cynodon dactylon* with Resistance to Nicosulfuron

*Cynodon dactylon* is a common weed as well as a turfgrass. In order to determine whether it has nicosulfuron resistant capability, nicosulfuron (400 mg/L) was sprayed, and it was observed after 10 days and found that there was no death for *Cynodon dactylon*, whereas all of the other control weeds including green bristlegrass, wild oats, *Amaranthus retroflexus*, humulus, purslane, *Monochoria vaginalis*, piemarker and nutgrass galingale herb were killed. Mesotrione (1000 mg/L) was also sprayed, it was observed after 10 days and found that there was no death for *Cynodon dactylon*, while other control weeds died due to the occurrence of whitening. It was demonstrated that *Cynodon dactylon* may have herbicide resistance gene.

EXAMPLE 2

Cloning of Resistance Gene

Plants usually have relatively large P450 gene family; for example, it has been found that there are more than 300 cytochrome P450 genes in *Arabidopsis thaliana* genome (Werck-Reichhart et al. (2000) Trends in Plant Science 5(3): 116-123). Although rice is not resistant to nicosulfuron, the genome sequence of rice has been known. Homologous genes of 3 cytochrome P450 genes (the polynucleotide sequences being NM_001057876, NM_001057880 and NM_001057877, respectively) are found in rice by molecular bioinformatics, in which one of these is a P450 gene participating in the degradation of herbicide bentazon (Pan et al., Plant Molecular Biology, 2006, 61: 933-943). It was found by comparison of these polynucleotide sequences that the sequences in some regions are relatively conservative.

The following PCR primers were designed according to the conservative region in the nucleotide sequence of the P450 gene in rice: 450F: 5'ACG GCC CGC ACT GGC GCA ACC TCC GCC G (SEQ ID NO:16) and 450R: 5'GTT CCT CAC GCC GAA CAC GTC GAA CCA CCG (SEQ ID NO:17).

Total mRNA was obtained by extraction from *Cynodon dactylon*, and cDNA was synthesized. PCR was carried out using the cDNA as template using the primers 450F and 450R. The PCR system and the PCR reaction conditions are as follows: 95° C. for 1 minute, 58° C. for 1 minute, 72° C. for 1 minute, repeated for 30 cycles. Then 72° C. for 5 minutes.

Accordingly, the PCR product was obtained. The PCR product was cloned into pMD18-T, and the DNA sequencing was further carried out. It was found that there were at least 2 kinds of fragments having different sequences in the PCR product. 2 cDNAs containing intact reading frame were obtained by cloning using RACE method. One of them was named as N-Z1 (SEQ ID NO: 2) and the other was named as N-Z2 (SEQ ID NO: 4). The protein polypeptide encoded by the N-Z1 reading frame is SEQ ID NO:1, and the protein polypeptide encoded by the N-Z2 reading frame is SEQ ID NO:3.

EXAMPLE 3

Construction of N-Z1 and N-Z2 Expression Cassettes Expressed in Rice

The DNA fragment that encodes N-Z1 was ligated to a maize ubiquitin-1 promoter (ZmUbi-1) at the 5' end and it was ligated to a 35S terminator of CaMV at the 3' end simultaneously by a common molecular biology method, so as to form an open reading frame which can be expressed in plants (with a HindIII at its 5'end and a KpnI site at the 3' end). The maize ubiquitin-1 promoter was obtained from maize genome by PCR. The PCR primers are ZmUbiF (5' GCGAAGCTTGCATGCCTACAGTGCAGCGTGACCC GGTCGTGC (SEQ ID NO:18), wherein the HindIII site is indicated in underline) and ZmUbiR (5' GTGGGAT CCTCTAGAGTCGACCTGCAGAAGTAACACCAAACA ACAG (SEQ ID NO:19), wherein the BamHI site is indicated in underline), respectively. Then, this expression cassette was cloned between the HindIII site and the KpnI site of pCambia 1300 to obtain the T-DNA vector pCam1300-N-Z1.

The DNA fragment that encodes N-Z2 was ligated to a maize ubiquitin-1 promoter (ZmUbi-1) at the 5' end and it was ligated to a 35S terminator of CaMV at the 3' end simultaneously by a common molecular biology method, so as to form an open reading frame which can be expressed in plants. An artificial gene capable of being expressed in plant cells was obtained (with a HindIII site at its 5'end and a KpnI site at its 3' end). The ubiquitin-1 promoter of maize was obtained from the maize genome by PCR. Then, this expression cassette was cloned between the HindIII site and the KpnI site of pCambia1300 to obtain the T-DNA vector pCam1300-N-Z2.

EXAMPLE 4

Transformation of Rice

The method for obtaining transgenic rice was implemented using existing technology (Lu Xiongbin, Gong zuxun, 1998, Life Science, 10: 125-131; Liu fan et al., 2003, Molecular Plant Breeding, 1:108-115). Ripe and plump "Xiushui 134" seeds were selected and deshelled, and the calli were induced and produced which would be used as transformation material. *Agrobacterium* containing target gene vectors pCam1300-N-Z1 and pCam1300-N-Z2 was taken and streaked onto a plate, and single colony was selected and inoculated to prepare *Agrobacterium* for transformation. The calli to be transformed were placed into *Agrobacterium* liquid (containing acetosyringone) with proper concentration, allowing the *Agrobacterium* to be conjugated to the surface of the calli, and then the calli were transferred to a coculture medium and cocultured for 2-3 days. The transformed calli were rinsed with aseptic water and transferred to a selective medium containing appropriate hygromycin, and cultured for screening for two months (subcultured one time during the period). The calli after being screened with good viability were transferred to a pre-differentiation medium and cultured for about 20 days, and then the pre-differentiated calli were transferred to a differential medium and irradiated with light for 14 hours for differentiation and sprouting. After 2-3 weeks, the regenerated plants having resistance were transferred to a rooting medium containing nicosulfuron (0.1 mg/L) for strengthening the seedling and growing roots, and then the regenerated plants were rinsed to remove agar and transferred into a greenhouse to be used as identification materials.

EXAMPLE 5

Determination of Herbicide Resistance Capability of Transgenic Rice 10 different transgenic rice strains obtained by pCam1300-N-Z1 vector transformation and non-transgenic strains of the same variety "XiuShui 134" were selected and planted in a greenhouse (at a temperature of 15° C.-25° C.), and nicosulfuron (Yu Nongle, zhejiang Gold-Ox pesticides LTD) was sprayed at 6 mg/square meter when the seedlings have a height of about 10 cm. After 10 days, it was found that all the non-transgenic strains died, whereas the transgenic strains have a death rate of 0%, in which 8 transgenic strains did not show any observable growth inhibition, and 2 strains have slow growth.

10 different transgenic rice strains obtained by pCam1300-N-Z1 vector transformation and non-transgenic strains of the same variety "XiuShui 134" were selected and planted in a greenhouse (at a temperature of 15° C.-25° C.), and mesotrione (10% mesotrione suspension, Syngenta) was sprayed at 15 mg/square meter when the seedlings have a height of about 10 cm. After 10 days, it was found that all the non-transgenic strains died, whereas the transgenic strains have a death rate of 0%, in which 3 transgenic strains did not show any observable growth inhibition, and 7 strains have slow growth.

10 different transgenic rice strains obtained by pCam1300-N-Z2 vector transformation and non-transgenic strains of the same variety "XiuShui 134" were selected and planted in the greenhouse (at a temperature of 15° C.-25° C.), and nicosulfuron was sprayed at 6 mg/square meter when the seedlings have a height of about 10 cm. After 10 days, it was found that all of the non-transgenic strains and the transgenic strains died, which demonstrated that N-Z2 had no nicosulfuron resistance capability.

10 different transgenic rice strains obtained by pCam1300-N-Z2 vector transformation and non-transgenic strains of the same variety "XiuShui 134" were selected and planted in the greenhouse (at a temperature of 15° C.-25° C.), and mesotrione was sprayed at 15 mg/square meter when the seedlings have a height of about 10 cm. After 10 days, it was found that all of the non-transgenic strains and the transgenic strains died, which demonstrated that N-Z2 had no mesotrione resistance capability.

EXAMPLE 6

Construction of Dicotyledonous Transformation Vector and Transformation of *Arabidopsis thaliana*

Vector Construction pCambia1300 vector was reconstructed as follows: the hygromycin resistant gene was removed using XhoI enzyme and then substituted for glyphosate-resistant EPSPS gene (nucleotide sequence being SEQ ID NO: 15) to obtain the vector pCambia1300-35S:G10. The expression cassette of N-Z1 is composed of 35S promoter of CaMV, N-Z1 gene and 35S terminator of CaMV, and a HindIII site was arranged at the 5' end of the expression cassette and a KpnI site was arranged at the 3' end. Then, this expression cassette was cloned between the HindIII site and KpnI site of an intermediate vector pCambia1300-35S:G10 to obtain the transformed vector pCambia1300-35 S/G10-35 S/N-Z1.

Transformation of *Arabidopsis thaliana*:

The *Agrobacterium* introduced with the pCambia1300-35 S/G10-35 S/N-Z1 vector was inoculated into a test tube containing YEP (containing yeast extract 10 g/L, peptone 10 g/L, NaCl 5 g/L) culture solution, followed by shaking at 3000 rpm overnight at 28° C. for about 30 hours, the bacteria activated via shaking were transferred into 300 mL of YEP and cultured at 28° C. at 300 rpm for about 14 hours, and the OD value was measured, and the bacterial cells can be collected in a 250 mL centrifuge bottle (sterilized) when the OD600 of the bacterial suspension reaches within the range of 1.5-3.0, and centrifuged at 4000 g at 4° C. for 10 min. The bacterial cells were diluted to OD600 of about 0.8-1.0 using 10% sugar (containing 0.02% silwet). The flowers were immersed in the resulting bacterial suspension for about 1 minute during transformation, and growth was allowed under weak light.

The seeds obtained from *Arabidopsis thaliana* infected by *Agrobacterium* were allowed to germinate and grow in *Arabidopsis thaliana* growth medium containing 0.5 mM glyphosate. The untransformed seeds cannot grow after germination due to the action of glyphosate, yellowed and died. However, the seeds that introduced with T-DNA can grow and develop, followed by flowering and harvesting seeds. A total of 35 individual glyphosate-resistant seedlings (T0 generation) were obtained, and the seeds thereof were harvested.

EXAMPLE 7

Determination of Herbicide Resistance Capability of Transgenic *Arabidopsis thaliana*

A total of 35 individual transformation lines were obtained using vector pCambia1300-35S/G10-35S/N-Z1. The T1 generation seedlings (obtained after the germination of T0 generation seeds) were sprayed with glyphosate diluted at 1:200 (41% aqueous solution of glyphosate isopropylamine salt, Xin'an chemical company) to remove the isolated plants without introduction of glyphosate-resistant gene. The survived plants were subjected to herbicide resistance test after growing to $4^{th}$-$6^{th}$ leaf stages.

Nicosulfuron resistance test: 10 plants for each line were sprayed with nicosulfuron (the dose is equal to 6 mg/square meter, the effective spraying concentration was 80 mg/L, and the product was Yu Nongle, Zhejiang Gold-Ox pesticides LTD). Non-transgenic recipient parent *Arabidopsis thaliana* was used as negative control. Their nicosulfuron resistance levels were evaluated 10 days after spraying nicosulfuron. The results showed that no obvious herbicide damage was observed in 21 transformation lines, 8 lines exhibited different degrees of growth inhibition, and 6 lines were killed. All of the non-transgenic recipient parent *Arabidopsis thaliana* died.

Mesotrione resistance test: 10 plants for each line were sprayed with mesotrione (the dose is equal to 15 mg/square meter, the effective spraying concentration was 200 mg/L, and the product was 10% mesotrione suspension, Syngenta). Non-transgenic recipient parent *Arabidopsis thaliana* was used as negative control. Their mesotrione resistant levels were evaluated 10 days after spraying mesotrione. The results showed that no obvious herbicide damage was found in 6 transformation lines, 18 plants exhibited a certain degree of whitening at the early stage, but most of them were recovered later, and 11 plants were killed. All of the non-transgenic recipient parent *Arabidopsis thaliana* died.

2,4-D resistance test: 10 plants for each line were sprayed with 2,4-D (the dose was equal to 150 mg/square meter, the spraying concentration was 1.4 g/L, and the product was soluble powder of 2-methyl-4-chlorophenoxyacetic acid sodium salt, Haiyan boda fine chemical Co., Ltd). Non-transgenic recipient parent *Arabidopsis thaliana* was used as negative control. Their resistance levels were evaluated 10 days after spraying 2,4-D. The results showed that no obvious herbicide damage was found in 27 transformation lines, and 8 lines exhibited different degrees of growth inhibition. All of the non-transgenic recipient parent *Arabidopsis thaliana* died.

Among others, the transformation line N-Z1-At6 had good resistance to the above 3 types of herbicides. The resistance capability of N-Z1-At6 to other herbicides was further tested. Atrazine (90% water dispersible granule, Syngenta), Dicamba (48% aqueous formulation, Syngenta), flumiclorac-pentyl (10% emulsifiable concentrate, Sumitomo Chemical Corporation), bentazon, penoxsulam, bensulfuron and tribenuron are respectively sprayed during the $4^{th}$-$6^{th}$ leaf stage. The result shows that the resistance level of N-Z1-At6 to these herbicide are obviously improved than the non-transgenic parental plants.

The transformation line N-Z1-At6 was further tested for the resistance to herbicide mixture. The results showed that the resistance of N-Z1-At6 to the mixture of mesotrione and nicosulfuron, the mixture of mesotrione and 2,4D, the mixture of flumiclorac-pentyl and 2,4D, and the mixture of bentazon and penoxsulam was obviously higher than that of non-transgenic control. The N-Z1-At6 also had significant resistance to the mixture of three herbicides including mesotrione, nicosulfuron and 2,4D.

The invention claimed is:

1. An expression cassette comprising a herbicide resistance gene operably linked to a heterologous promoter, wherein said herbicide resistance gene comprises
a nucleic acid sequence encoding a protein having an amino acid sequence with at least 95% sequence identity to SEQ ID NO: 1, wherein the encoded protein confers herbicide resistance activity to a plant when the nucleic acid sequence is expressed in said plant, wherein said herbicide resistance comprises resistance to at least one of the following types of herbicides: acetolactate synthase (ALS)-inhibiting herbicides, protoporphyrinogen oxidase (PPO)-inhibiting herbicides, p-hydroxyphenylpyruvate dioxygenase (HPPD)-inhibiting herbicides, photosystem II-inhibiting herbicides, and synthetic auxin herbicides.

2. The expression cassette according to claim 1, characterized in that the encoded protein thereof is capable of resulting in the resistance to at least two herbicides respectively belonging to at least two of the following types of herbicides: acetolactate synthase (ALS)-inhibiting herbicides, protoporphyrinogen oxidase (PPO)-inhibiting herbicides, p-hydroxyphenylpyruvate dioxygenase (HPPD)-inhibiting herbicides, photosystem II-inhibiting herbicides, and synthetic auxin herbicides.

3. The expression cassette according to claim 1, characterized in that the encoded protein thereof is capable of resulting in the resistance to at least three herbicides respectively belonging to at least three of the following types of herbicides: acetolactate synthase (ALS)-inhibiting herbicides, protoporphyrinogen oxidase (PPO)-inhibiting herbicides, p-hydroxyphenylpyruvate dioxygenase (HPPD)-inhibiting herbicides, photosystem II-inhibiting herbicides, and synthetic auxin herbicides.

4. The expression cassette according to claim 1, characterized in that the encoded protein thereof is capable of resulting in the resistance to at least four herbicides respectively belonging to at least four of the following types of herbicides: acetolactate synthase (ALS)-inhibiting herbicides, protoporphyrinogen oxidase (PPO)-inhibiting herbicides, p-hydroxyphenylpyruvate dioxygenase (HPPD)-inhibiting herbicides, photosystem II-inhibiting herbicides, and synthetic auxin herbicides.

5. The expression cassette according to claim 1, characterized in that the encoded protein thereof is capable of resulting in the resistance to at least five herbicides respectively belonging to at least five of the following types of herbicides: acetolactate synthase (ALS)-inhibiting herbicides, protoporphyrinogen oxidase (PPO)-inhibiting herbicides, p-hydroxyphenylpyruvate dioxygenase (HPPD)-inhibiting herbicides, photosystem II-inhibiting herbicides, and synthetic auxin herbicides.

6. The expression cassette according to claim 1, characterized in that the amino acid sequence of the encoded protein thereof is SEQ ID NO: 1.

7. A DNA vector, comprising the expression cassette according to claim 1.

8. A method for producing transgenic herbicide-resistant plants, said method comprising:
introducing the expression cassette of claim 1 into a plant; and
culturing the plant comprising said expression cassette.

9. The method of claim 8, characterized in that the plants are monocotyledons or dicotyledons.

10. The method of claim 9, characterized in that
said monocotyledons are rice, maize, wheat, barley, sorghum or turfgrass; and
said dicotyledons include soybean, rape, cotton, sunflower or potato.

11. A method for preventing and controlling weeds in a transgenic plant using herbicides, said method comprising:
introducing the expression cassette of claim 1 into a plant to produce a transgenic plant;
culturing the transgenic plant comprising said expression cassette; and
applying at least one herbicide to the area where the transgenic plant is growing, wherein said herbicide is selected from the group consisting of: acetolactate synthase (ALS)-inhibiting herbicides, protoporphyrinogen oxidase (PPO)-inhibiting herbicides, p-hydroxyphenylpyruvate dioxygenase (HPPD)-inhibiting herbicides, photosystem II-inhibiting herbicides, and synthetic auxin herbicides, and
wherein said transgenic plant is resistant to said herbicide.

12. The method of claim 11, which is characterized in that at least two herbicides belonging to the following types of herbicides are mixed for use: acetolactate synthase (ALS)-inhibiting herbicides, protoporphyrinogen oxidase (PPO)-inhibiting herbicides, p-hydroxyphenylpyruvate dioxygenase (HPPD)-inhibiting herbicides, photosystem II-inhibiting herbicides, and synthetic auxin herbicides.

* * * * *